(12) United States Patent
Scherl et al.

(10) Patent No.: US 11,330,830 B2
(45) Date of Patent: May 17, 2022

(54) CALCIUM OXALATE TITRATION TEST KITS AND PET FOOD COMPOSITIONS

(71) Applicant: Hill's Pet Nutrition, Inc., Topeka, KS (US)

(72) Inventors: Dale Scherl, Lawrence, KS (US); Dennis Jewell, Lawrence, KS (US); Jeffrey Brockman, Lawrence, KS (US); Stephen Davidson, Topeka, KS (US); Christina Golder, Topeka, KS (US); Albert Avila, Overland Park, KS (US)

(73) Assignee: Hills Pet Nutrition, Inc., Topeka, KS (US)

( * ) Notice: Subject to any disclaimer, the term of this patent is extended or adjusted under 35 U.S.C. 154(b) by 428 days.

(21) Appl. No.: 16/474,098

(22) PCT Filed: Dec. 8, 2017

(86) PCT No.: PCT/US2017/065311
§ 371 (c)(1),
(2) Date: Jun. 27, 2019

(87) PCT Pub. No.: WO2018/125539
PCT Pub. Date: Jul. 5, 2018

(65) Prior Publication Data
US 2020/0284812 A1    Sep. 10, 2020

Related U.S. Application Data

(63) Continuation-in-part of application No. PCT/US2016/068651, filed on Dec. 27, 2016.

(51) Int. Cl.
*A23K 20/158* (2016.01)
*A23K 50/40* (2016.01)
(Continued)

(52) U.S. Cl.
CPC ............ *A23K 20/158* (2016.05); *A23K 50/40* (2016.05); *G01N 33/52* (2013.01); *G01N 33/84* (2013.01); *G01N 2800/348* (2013.01)

(58) Field of Classification Search
CPC ...... A23K 20/158; A23K 50/40; A23K 50/42; G01N 33/52; G01N 33/84; G01N 2800/348; A61P 13/00; A61P 13/04
See application file for complete search history.

(56) References Cited

U.S. PATENT DOCUMENTS

| 3,798,000 | A | * | 3/1974 | Helger | G01N 33/84 436/79 |
| 4,183,729 | A | | 1/1980 | Randolph | |
| 4,399,003 | A | * | 8/1983 | Sarig | G01N 33/84 204/418 |

(Continued)

FOREIGN PATENT DOCUMENTS

| CN | 1570635 A | 1/2005 |
| CN | 1888887 A | 1/2007 |

(Continued)

OTHER PUBLICATIONS

Grauer, "Feline Struvite & Calcium Oxalate Urolithiasis," Today's Veterinary Practice, Sep./Oct. 2015, pp. 14-20. (Year: 2015).*

(Continued)

*Primary Examiner* — Jennifer Wecker
*Assistant Examiner* — Michael Paul Shimek

(57) ABSTRACT

Described herein are kits for assessing the calcium oxalate titration test of an animal as well as methods for predicting the risk of calcium oxalate stone formation. Further described herein are methods and compositions for—inter alia—lowering the specific gravity of urine and lowering the calcium oxalate titration test in felines. In particular, diets and methods utilizing certain amounts and ratios of arachi- (Continued)

donic acid (AA), eicosapentaenoic acid (EPA) and docosahexaenoic acid (DHA) are disclosed herein.

15 Claims, 15 Drawing Sheets

(51) Int. Cl.
    *G01N 33/52*     (2006.01)
    *G01N 33/84*     (2006.01)

(56) References Cited

U.S. PATENT DOCUMENTS

| | | | |
|---|---|---|---|
| 5,366,899 | A | 11/1994 | Shabalin et al. |
| 6,027,939 | A | 2/2000 | Grases Freixedas et al. |
| 6,946,488 | B2 | 9/2005 | Hayek et al. |
| 8,252,742 | B2 | 8/2012 | Yamka et al. |
| 9,492,491 | B1 | 11/2016 | Hayer et al. |
| 9,884,035 | B2 | 2/2018 | Brockman et al. |
| 2002/0081743 | A1 | 6/2002 | Gottlieb |
| 2010/0236975 | A1 | 9/2010 | Yamka |
| 2010/0304003 | A1 | 12/2010 | Inke |
| 2012/0129785 | A1 | 5/2012 | Fleuranges et al. |
| 2013/0032494 | A1 | 2/2013 | Gomila Munoz et al. |
| 2015/0204880 | A1 | 7/2015 | Chiang et al. |
| 2015/0297545 | A1 | 10/2015 | Rimer et al. |

FOREIGN PATENT DOCUMENTS

| | | |
|---|---|---|
| ES | 2003686 | 11/1988 |
| JP | S5713827 A | 1/1982 |
| JP | S57154058 A | 9/1982 |
| JP | H029310 A | 1/1990 |
| JP | H02284061 A | 11/1990 |
| JP | H0783931 A | 3/1995 |
| JP | H08105886 A | 4/1996 |
| JP | 2007116977 A | 5/2007 |
| JP | 2009501342 A | 1/2009 |
| JP | 2017500844 A | 1/2017 |
| JP | 2018075042 A | 5/2018 |
| JP | 2020007320 A | 1/2020 |
| SU | 1629846 A1 | 2/1991 |
| WO | 2001/008270 | 2/2001 |
| WO | 2003/103579 | 12/2003 |
| WO | 2011/011472 | 1/2011 |
| WO | 2013/017725 A1 | 2/2013 |
| WO | 2018/117129 A1 | 6/2018 |

OTHER PUBLICATIONS

Costa, 2011, "A Guide to Urinalysis," Feline Update, Retrieved from the Internet: URL:http://www.langfordvets.co.uk/sites/default/files/Feline%20Update%20Autumn%202011%20revised%20030713.pdf [retrieved on Feb. 5, 2018].

Hand et al., eds., 2000, Small Animal Clinical Nutrition, 4th ed., p. 702.

Hess et al., 2000, "Citrate determines calcium oxalate crystallization kinetics and crystal morphology-studies in the presence of Tamm-Horsfall protein of a healthy subject and a severely recurrent calcium stone former," Nephrology Dialysis Transplantation 15(3):366-374.

International Search Report and Written Opinion of the International Searching Authority in International Application No. PCT/US2013/069659, dated Jul. 31, 2014.

International Search Report and Written Opinion of the International Searching Authority in International Application No. PCT/US2016/068651, dated Feb. 15, 2017.

International Search Report and Written Opinion of the International Searching Authority in International Application No. PCT/US2017/065311, dated Apr. 18, 2018.

Kerr et al., 2013 "Companion animals symposium : dietary management of feline lower urinary tract symptoms," Journal of Animal Science 91(6):2965-2975.

Lulich et al., 2004, "Cystocentesis: Lessons from Thirty Years of Clinical Experience," Procedures Pro [Retrieved from the Internet: Feb. 6, 2018] URL:https://www.cliniciansbrief.com/sites/default/files/sites/cliniciansbrief com/files/cystocentesis.pdf.

Purina Veterinary Diets, 2014, "NF KidNey Function Brand Canine and Feline Formulas," retrieved from the Internet: URL:https://www.purinaproplanvets.com/media/1192/canine_nf.pdf.

Rayne, 2016, "Adult Health-RSS," Rayne Clinical Nutrition 1-5, Retrieved from the Internet: URL:http://www.raynecanada.ca/s/FE_AdultRSS_Oct2416.pdf.

Rodgers et al., 1994, "Effect of urinary macromolecules and chondroitin sulphate on calcium oxalate crystallization in urine," Medline/NLM Database entry Scanning Microscopy 8(1):71-77.

Laube et al., "A new approach to calculate the risk of calcium oxalate crystallization from unprepared native urine", Urological Research, 2000, vol. 28, No. 4, pp. 274-280.

Ryall et al., "A Method for Studying Inhibitory Activity in Whole Urine", Urological Research, 1985, vol. 13, No. 6, pp. 285-289.

\* cited by examiner

| | oxalate concentrations (150 ml) | | | | | | | | | | | |
|---|---|---|---|---|---|---|---|---|---|---|---|---|
| sample 1 | A | B=A/2 | C=B/2 | D=C/2 | E=D/2 | F=E/2 | G=F/2 | H=G/2 | I=H/2 | J=I/2 | K=J/2 | L=K/2 |
| sample 2 | A | B=A/2 | C=B/2 | D=C/2 | E=D/2 | F=E/2 | G=F/2 | H=G/2 | I=H/2 | J=I/2 | K=J/2 | L=K/2 |
| sample 3 | A | B=A/2 | C=B/2 | D=C/2 | E=D/2 | F=E/2 | G=F/2 | H=G/2 | I=H/2 | J=I/2 | K=J/2 | L=K/2 |
| sample 4 | A | B=A/2 | C=B/2 | D=C/2 | E=D/2 | F=E/2 | G=F/2 | H=G/2 | I=H/2 | J=I/2 | K=J/2 | L=K/2 |
| sample 5 | A | B=A/2 | C=B/2 | D=C/2 | E=D/2 | F=E/2 | G=F/2 | H=G/2 | I=H/2 | J=I/2 | K=J/2 | L=K/2 |
| sample 6 | A | B=A/2 | C=B/2 | D=C/2 | E=D/2 | F=E/2 | G=F/2 | H=G/2 | I=H/2 | J=I/2 | K=J/2 | L=K/2 |
| sample 7 | A | B=A/2 | C=B/2 | D=C/2 | E=D/2 | F=E/2 | G=F/2 | H=G/2 | I=H/2 | J=I/2 | K=J/2 | L=K/2 |
| sample 8 | A | B=A/2 | C=B/2 | D=C/2 | E=D/2 | F=E/2 | G=F/2 | H=G/2 | I=H/2 | J=I/2 | K=J/2 | L=K/2 |

100mL of the oxalate solutions should be added to 100mL urine to avoid locally high oxalate contrations during mixing

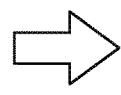

| | oxalate concentrations (100ml) + 100ml urine | | | | | | | | | | | |
|---|---|---|---|---|---|---|---|---|---|---|---|---|
| sample 1 | A/2 | B/2 | C/2 | D/2 | E/2 | F/2 | G/2 | H/2 | I/2 | J/2 | K/2 | L/2 |
| sample 2 | A/2 | B/2 | C/2 | D/2 | E/2 | F/2 | G/2 | H/2 | I/2 | J/2 | K/2 | L/2 |
| sample 3 | A/2 | B/2 | C/2 | D/2 | E/2 | F/2 | G/2 | H/2 | I/2 | J/2 | K/2 | L/2 |
| sample 4 | A/2 | B/2 | C/2 | D/2 | E/2 | F/2 | G/2 | H/2 | I/2 | J/2 | K/2 | L/2 |
| sample 5 | A/2 | B/2 | C/2 | D/2 | E/2 | F/2 | G/2 | H/2 | I/2 | J/2 | K/2 | L/2 |
| sample 6 | A/2 | B/2 | C/2 | D/2 | E/2 | F/2 | G/2 | H/2 | I/2 | J/2 | K/2 | L/2 |
| sample 7 | A/2 | B/2 | C/2 | D/2 | E/2 | F/2 | G/2 | H/2 | I/2 | J/2 | K/2 | L/2 |
| sample 8 | A/2 | B/2 | C/2 | D/2 | E/2 | F/2 | G/2 | H/2 | I/2 | J/2 | K/2 | L/2 |

100 μl of the oxilate solutions added to 100μl urine

FIG. 1 (CONT.)

URINE PLATE

100μl urine + 100μl from corresponding well of (e.g.) citrate plate + 100μl from corresponding well of oxalate plate

| | A | B | C | D | E | F | G | H | I | J | K | L |
|---|---|---|---|---|---|---|---|---|---|---|---|---|
| sample 1 | A/3+M/3 | B/3+M/3 | C/3+M/3 | D/3+M/3 | E/3+M/3 | F/3+M/3 | G/3+M/3 | H/3+M/3 | I/3+M/3 | J/3+M/3 | K/3+M/3 | L/3+M/3 |
| sample 1 | A/3+N/3 | B/3+N/3 | C/3+N/3 | D/3+N/3 | E/3+N/3 | F/3+N/3 | G/3+N/3 | H/3+N/3 | I/3+N/3 | J/3+N/3 | K/3+N/3 | L/3+N/3 |
| sample 1 | A/3+O/3 | B/3+O/3 | C/3+O/3 | D/3+O/3 | E/3+O/3 | F/3+O/3 | G/3+O/3 | H/3+O/3 | I/3+O/3 | J/3+O/3 | K/3+O/3 | L/3+O/3 |
| sample 1 | A/3+P/3 | B/3+P/3 | C/3+P/3 | D/3+P/3 | E/3+P/3 | F/3+P/3 | G/3+P/3 | H/3+P/3 | I/3+P/3 | J/3+P/3 | K/3+P/3 | L/3+P/3 |
| sample 1 | A/3+Q/3 | B/3+Q/3 | C/3+Q/3 | D/3+Q/3 | E/3+Q/3 | F/3+Q/3 | G/3+Q/3 | H/3+Q/3 | I/3+Q/3 | J/3+Q/3 | K/3+Q/3 | L/3+Q/3 |
| sample 1 | A/3+R/3 | B/3+R/3 | C/3+R/3 | D/3+R/3 | E/3+R/3 | F/3+R/3 | G/3+R/3 | H/3+R/3 | I/3+R/3 | J/3+R/3 | K/3+R/3 | L/3+R/3 |
| sample 1 | A/3+S/3 | B/3+S/3 | C/3+S/3 | D/3+S/3 | E/3+S/3 | F/3+S/3 | G/3+S/3 | H/3+S/3 | I/3+S/3 | J/3+S/3 | K/3+S/3 | L/3+S/3 |
| sample 1 | A/3+T/3 | B/3+T/3 | C/3+T/3 | D/3+T/3 | E/3+T/3 | F/3+T/3 | G/3+T/3 | H/3+T/3 | I/3+T/3 | J/3+T/3 | K/3+T/3 | L/3+T/3 |

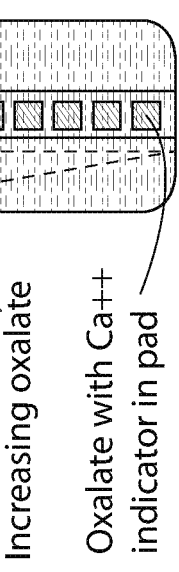
FIG. 8A
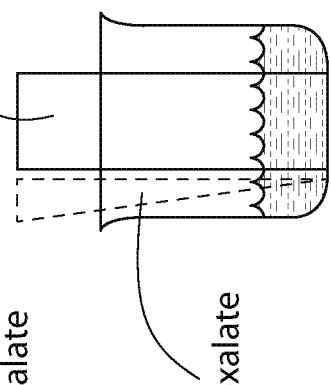
FIG. 8B
FIG. 8C
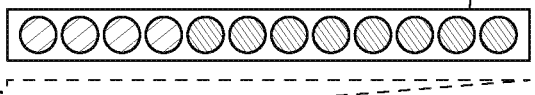
FIG. 8D
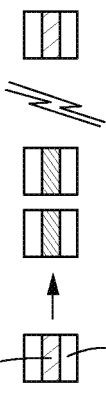
FIG. 8E

CALCIUM OXALATE TITRATION TEST KITS AND PET FOOD COMPOSITIONS

BACKGROUND

The domestic cat (*Felis domesticus*) lives successfully in desert conditions and is adapted to retain water by producing urine which is very concentrated compared to most other mammals. Producing highly concentrated urine, however, can have deleterious effects, such as enhancing development of urinary stones and other less well defined urinary tract conditions such as feline idiopathic cystitis. A feline urinary tract condition often due to poor hydration is sometimes referred to as Feline Lower Urinary Tract Disease (FLUTD).

FLUTD can be a life-threatening condition for cats. In particular, a problem that cat owners face with FLUTD is that the disease is life-threatening to the cat by the time the symptoms are noticeable to the owner. Crystals can precipitate in the cat's urinary tract as stones and obstruct the flow of urine. Types of stones include struvite, calcium oxalate, urate, cystine, calcium phosphate, and silicate. Struvite and calcium oxalate stones are by far the most common in cats. If left untreated, a "blocked" cat will die, as the urine backs up and damages the kidneys, and toxins accumulate in the blood.

If the cat can be induced to drink more, this can dilute the urine and thereby ameliorate feline urinary conditions resulting from low hydration. This dilution acts at two levels: first, by reducing the electrolyte concentration in the urine (as-suming the cat is not drinking more simply to compensate for higher dietary salt), and then by increasing duriesis and therefore reducing the amount of time spent by the urine in the bladder. Cats generally drink only about 30 milliliters of water per kilo of body weight per day, and it is difficult to increase spontaneous drinking. Providing moist food helps to increase water intake in an animal that does not drink very much, but may not be sufficient, either because there is still not enough water ingested or because it does not sufficiently increase micturition. In addition, cats exhibiting a urological syndrome are often obese or carry excess weight. Thus, when it is desired to treat urinary disorders, and in particular FLUTD, providing a moist food may be preferable, but it is not sufficient, i.e., the food does not provide sufficient hydration, may not be accepted by the cat, or even may induce an additional excess weight and/or obesity if the amount consumed is poorly controlled.

There exists today a need for methods and compositions to increase hydration in cats, thereby treating, reducing, inhibiting, or ameliorating urinary conditions such as FLUTD. The incorporation of certain omega-3 polyunsaturated fatty acids such as docosahexaenoic acid ("MIA") and eicosapentaenoic acid ("EPA") in pet food compositions is generally known. And, while certain cat foods are known to contain both omega-3 and omega-6 polyunsaturated fatty, acids, there does not appear to be any teaching or suggestion that fatty acids are responsible/play a critical role in hydration levels.

BRIEF SUMMARY

It has been surprisingly discovered that controlling the ratio of certain omega-3 and omega-6 polyunsaturated fatty acids in cat food will result in a lowered specific gravity of cat urine and a lowered risk of calcium oxalate stone formation as indicated by the calcium oxalate titration test ("COTT"), also known as the calcium oxalate risk index ("CORI"). In particular, a ratio of arachidonic acid ("AA") to EPA+DHA [AA:(EPA+DHA)] of less than 1 lowers the specific gravity of cat urine and reduces COTT in both young and mature adult cats without dehydrating the animal.

In some embodiments, the present disclosure concerns a method of lowering the specific gravity of urine and the COTT value in a cat comprising feeding the cat a food composition comprising AA, EPA and DHA wherein the ratio of AA:(EPA+DHA) ranges from 0.1:1 to 0.9:1 and the combined amount of AA, EPA and DHA is 0.05 to 1.5% dry weight.

In some embodiments, the present disclosure concerns a method of lowering the specific gravity of urine and the COTT value in a cat comprising feeding the cat a food composition comprising AA, EPA and DHA wherein the ratio of AA:(EPA+DHA) ranges from 0.1:1 to 0.9:1, the combined amount of AA, EPA and DHA is 0.05 to 1.5% dry weight, and the food composition has a total omega-6 fatty acids to total omega-3 fatty acids ratio (n6:n3) ranging from about 2:1 to about 8:1.

In some embodiments, the present disclosure concerns method of treating a disease or condition in a cat resulting from low hydration comprising feeding the cat a food containing AA, EPA and DHA wherein the ratio of AA:(EPA+DHA) ranges from 0.1:1 to 0.9:1 and the combined amount of AA, EPA and DHA is 0.05 to 1.5% dry weight.

In some embodiments, the present disclosure concerns method of treating a disease or condition in a cat resulting from low hydration comprising feeding the cat a food containing AA, EPA and DHA wherein the ratio of AA:(EPA+DHA) ranges from 0.1:1 to 0.9:1, the combined amount of AA, EPA and DHA is 0.05 to 1.5% dry weight, and the food composition has a total omega-6 fatty acids to total omega-3 fatty acids ratio (n6:n3) ranging from about 2:1 to about 8:1.

In some embodiments, the present disclosure concerns a palatable, nutritionally complete cat food composition comprising AA, EPA and MIA in an amount effective to improve the hydration in a cat, wherein the food composition, together with water, is palatable and nutritionally complete as a sole diet for the cat, and wherein the ratio of AA:(EPA DHA) ranges from 0.1:1 to 0.9:1, and the combined amount of AA, EPA and DHA is 0.05 to 1.5% dry weight.

In further embodiments, the present disclosure concerns a palatable, nutritionally complete cat food composition comprising AA, EPA and DHA in an amount effective to improve the hydration in a cat, wherein the food composition, together with water, is palatable and nutritionally complete as a sole diet for the cat, and wherein the ratio of AA:(EPA+DHA) ranges from 0.1:1 to 0.9:1 and the combined amount of AA, EPA and DHA is 0.05 to 1.5% dry weight and wherein the compositions have other omega-3 and omega-6 fatty acids incorporated therein. In such embodiments, the food composition has a total omega-6 fatty acids to total omega-3 fatty acids ratio (n6:n3) ranging from about 2:1 to about 8:1.

Further embodiments disclosed herein include diagnostic kits for identifying an animal, such as a feline, as being at elevated risk of developing a disease or condition resulting from low hydration, such as FLUTD, the diagnostic kits comprising at least one alkali metal oxalate sample, a means for detecting calcium ion concentration, optionally a container for a urine sample, and instructions for using the kit. In certain embodiments, the diagnostic kit is for identifying felines as being at an elevated risk for the formation of calcium oxalate stones. In certain embodiments disclosed herein, the diagnostic kits comprise at least one alkali metal oxalate sample that may be contacted with urine from the animal, a means for detecting calcium ion concentration in the at least one alkali metal oxalate sample, optionally a container for a urine sample, and instructions for using the kit.

According to certain embodiments of the diagnostic kits disclosed herein, the diagnostic kit comprises a plurality of alkali metal oxalate samples, wherein at least one of the alkali metal oxalate samples comprises a different concentration of alkali metal oxalate from at least one other alkali metal oxalate sample. In certain embodiments, the alkali metal oxalate is sodium oxalate, and in certain embodiments, the diagnostic kit further comprises at least one modifier of calcium oxalate, such as salts, metal ions, small organic compounds, amino acids, peptides, proteins, nucleotides, polynucleotides, saccharides, oligosaccharides, metabolites, and combinations thereof.

In certain embodiments, the means for detecting calcium ion concentration is at least one calcium-specific reporter dye, such as, for example, fluo-3, fluo-4, fluo-4FF, fluo-5F, mag-fluo-4, fura-2, indo-1, calcium green-1, calcium orange, calcium crimson, fura red, calcein, Oregon green, rhod-1, rhod-2, rhod-3, x-rhod-5F, x-rhod, bapta-1, bapta-2, bapta-6F, dextran-linked indicators, phthalein purple, and derivatives thereof.

In certain embodiments of the diagnostic kits disclosed herein, the at least one alkali metal oxalate sample is deposited on a surface, such as a card or paper, and in certain embodiments there is a plurality of alkali metal oxalate samples deposited on spaced-apart regions on the surface or, according to certain embodiments, deposited in a concentration gradient on the surface. According to certain embodiments, the plurality of alkali metal oxalate samples is deposited in wells of a well plate, such as a 96-well plate.

According to another embodiment disclosed herein, the plurality of alkali metal oxalate samples and the means for detecting calcium ion concentration are inside capillary channels of a multichannel plate, wherein the capillary channels of the multichannel plate are interconnected to a channel for receiving a urine sample. In yet a further embodiment of the diagnostic kits disclosed herein, the multichannel plate further comprises at least one capillary channel that comprises a means for detecting calcium ion concentration and is substantially free of oxalate.

In certain embodiments disclosed herein, there is a diagnostic kit for identifying an animal, such as a feline, as being at elevated risk of developing a disease or condition resulting from low hydration, comprising (1) at least one first container for holding a urine sample comprising at least one calcium-specific reporter dye and substantially free of oxalate; (2) at least one second container for holding a urine sample comprising at least one calcium-specific reporter dye and an alkali metal oxalate sample; and (3) a chart for comparing color of urine samples added to the first and second containers, wherein the colors on the chart are colors known to be observed for an alkali metal oxalate concentration or the absence of alkali metal oxalate, a concentration of free calcium ions, and a calcium-specific reporter dye.

A further embodiment disclosed herein is a diagnostic kit for identifying an animal, such as a feline, as being at elevated risk of developing a disease or condition resulting from low hydration, comprising a capillary tube comprising a thin-layer chromatography style matrix comprising at least one calcium-specific dye reporter and a plurality of alkali metal oxalate samples deposited in a gradient inside the capillary tube.

In another embodiment disclosed herein, there is a cystocentesis syringe for identifying an animal, such as a feline, as being at elevated risk of developing a disease or condition resulting from low hydration, comprising: (1) an internal chamber capable of receiving a urine sample; (2) at least one reaction chamber connected to the internal chamber; and (3) at least one hole between the internal chamber and the at least one reaction chamber, where the at least one reaction chamber comprises at least one calcium-specific dye reporter.

Further disclosed herein are methods for predicting the risk of calcium oxalate stone formation in the urinary tract of an animal, such as a feline, the method comprising preparing a plurality of alkali metal oxalate samples, wherein at least one sample comprises a concentration of alkali metal oxalate that is different from the concentration of alkali metal oxalate of at least one other sample; reacting a known volume of urine sample from the animal with the alkali metal oxalate samples; and determining the minimum concentration of alkali metal oxalate required to precipitate calcium oxalate, wherein a lower minimum concentration of alkali metal oxalate required to precipitate the calcium oxalate is associated with a higher risk of calcium oxalate stone formation in the urinary tract of the animal. In certain embodiments of the disclosure, the methods further comprise incubating at least one sample formed from the reaction of a known volume of urine and the alkali metal oxalate with a modifier of calcium oxalate, such a potassium citrate. In certain embodiments, the minimum concentration of alkali metal oxalate required to precipitate calcium oxalate is determined with a calcium-specific reporter dye, such as phthalein purple. In certain embodiments, the method further comprises a step of treating the animal who has been identified as having a higher risk of calcium oxalate stone formation in the urinary tract with an effective amount of a composition comprising AA, EPA and DHA wherein the ratio of AA:(EPA DHA) ranges from 0.1:1 to 0.9:1 and the combined amount of AA, EPA and DHA is 0.05 to 1.5% dry weight.

Yet a further embodiment is directed to a method of treating an animal, such as a feline, the method comprising the steps of administering an effective amount of a composition comprising AA, EPA and DHA wherein the ratio of AA:(EPA+DHA) ranges from 0.1:1 to 0.9:1 and the combined amount of AA, EPA and DHA is 0.05 to 1.5% dry weight to the animal, wherein the animal, prior to the administering step, has been identified as being at a higher risk of calcium oxalate stone formation in the urinary tract of the animal by a method comprising preparing a plurality of alkali metal oxalate samples, wherein at least one sample comprises a concentration of alkali metal oxalate that is different from the concentration of alkali metal oxalate of at least one other sample; reacting a known volume of urine sample from the animal with the alkali metal oxalate samples; and determining the minimum concentration of alkali metal oxalate required to precipitate calcium oxalate, wherein a lower minimum concentration of alkali metal oxalate required to precipitate the calcium oxalate is associated with a higher risk of calcium oxalate stone formation in the urinary tract of the animal.

Another embodiment is directed to a method for determining a minimum concentration of alkali metal oxalate required to precipitate calcium oxalate in a urine sample from an animal, such as a feline, the method comprising reacting a known volume of urine sample from the animal with a plurality of alkali metal oxalate samples, wherein at least one sample comprises a concentration of alkali metal oxalate that is different from the concentration of alkali metal oxalate of at least one other sample; and determining the minimum concentration of alkali metal oxalate required to precipitate calcium oxalate. In certain embodiments of the disclosure, the methods further comprise incubating at least one sample formed from the reaction of a known volume of urine and the alkali metal oxalate with a modifier of calcium oxalate, such a potassium citrate. In certain embodiments, the minimum concentration of alkali metal oxalate required to precipitate calcium oxalate is determined with a calcium-specific reporter dye, such as phthalein purple. In certain embodiments, the method further comprises before the reacting step, a step of preparing the plurality of alkali metal oxalate samples.

Further areas of applicability of the present invention will become apparent from the detailed description provided hereinafter. It should be understood that the detailed description and specific examples, while indicating preferred embodiments of the disclosed subject matter, are intended for purposes of illustration only and are not intended to limit the scope of the disclosure.

BRIEF DESCRIPTION OF THE DRAWINGS

The present invention will become more fully understood from the detailed description and the accompanying drawings, wherein:

FIG. 2C depicts 100 µL aliquots of urine added to the wells of another multi-well plate; and 100 µL aliquots taken from the wells of the oxalate plate and 100 µL aliquots taken from the wells of the citrate plate and added to the corresponding wells of the urine plate. Each well in the final multi-well plate now contains specific concentrations of citrate and oxalate in a specific volume of urine.

FIG. 4 shows a plot demonstrating the correlation between the amount of oxalate added in a traditional titration method and the concentration of oxalate in the last clear well in the method of the invention.

FIGS. 8A-E are schematics of kits according to the present invention. FIG. 8A shows an embodiment comprising a TLC slide with a $Ca^{2+}$ indicator and a single uniform concentration of oxalate. FIG. 8B shows an embodiment comprising a TLC slide with a $Ca^{2+}$ indicator and a gradient of concentration of oxalate. FIG. 8C shows an embodiment with a "pH style" paper, wherein oxalate and $Ca^{2+}$ indicator are provided in pads comprising different concentrations of oxalate. FIGS. 8D and 8E show top and side views respectively of an embodiment comprising a strip of wells, each well comprising oxalate with $Ca^{2+}$ indicator in liquid, gel or solid form. The contents of the wells may be covered with an inert water-soluble film.

DETAILED DESCRIPTION

Figure 1:
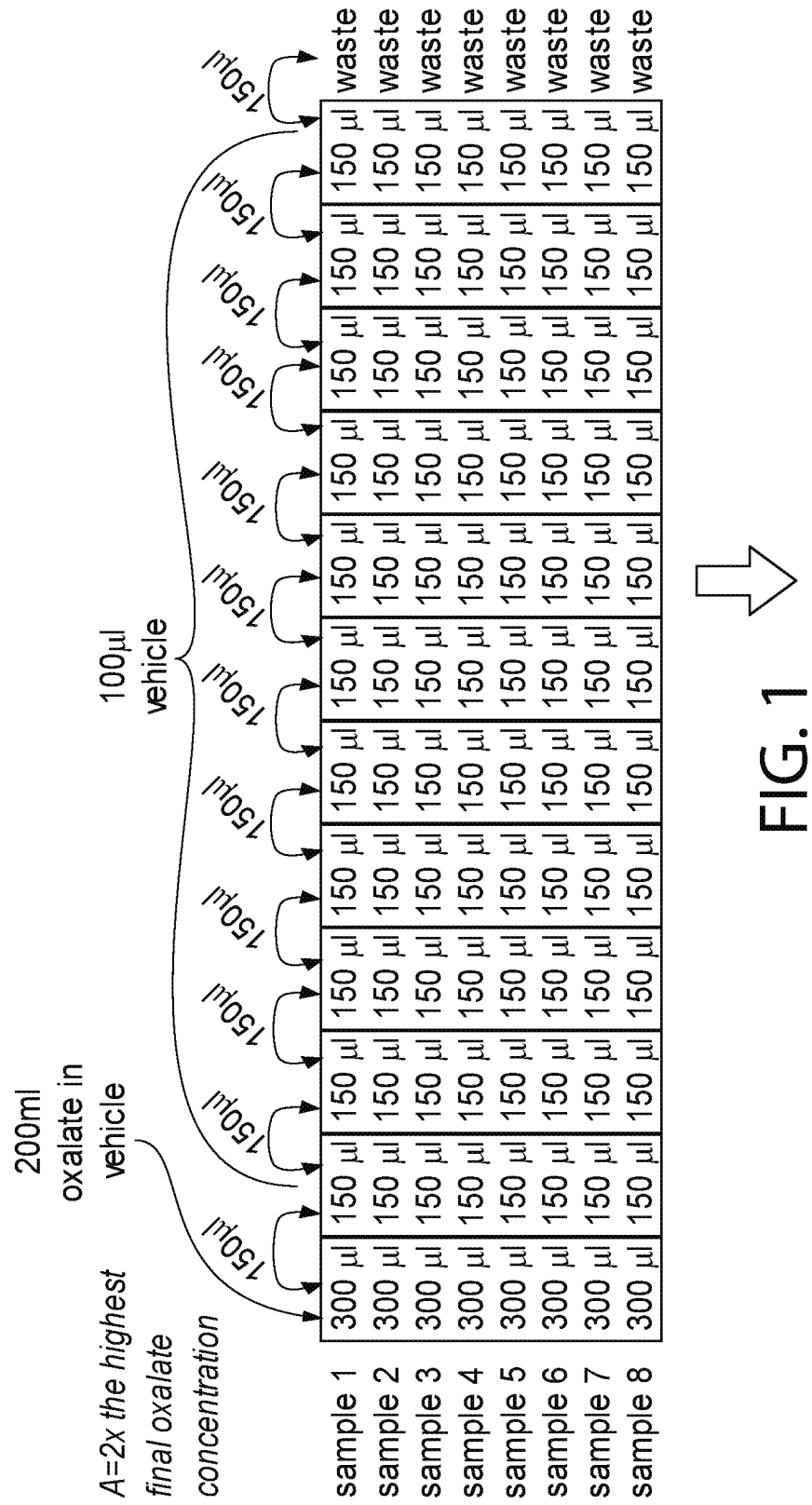
FIG. 1 shows an embodiment of the invention wherein a multi-well plate comprising a number of alkali metal oxalate solutions comprising different concentrations of alkali metal oxalate are prepared by serial dilution of an alkali metal oxalate solution across the rows of the multi-well plate. 100 µL aliquots of urine are added to the wells of another multi-well plate, and 100 µL aliquots are taken from the wells of the oxalate plate and added to the corresponding wells of the urine plate.

The following description of the preferred embodiment(s) is merely exemplary in nature and is in no way intended to limit the subject matter of the present disclosure, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls. Unless otherwise specified, all percentages and amounts expressed herein and elsewhere in the specification should be understood to refer to percentages by weight. All percentages expressed herein are on a weight by dry matter basis unless specifically stated otherwise.

In the context of the disclosure, the term "treating" or "treatment", as used herein, means reversing, alleviating, mitigating or inhibiting the progress of the disorder or condition to which such term applies, or one or more symptoms of such disorder or condition. As used herein and in the appended claims, the singular forms "a", "an", and "the" include plural reference unless the context clearly dictates otherwise.

In the context of the disclosure, the term "about" can refer to a variation of ±0.01%, ±0.1%, ±0.5%, ±1%, ±5%, ±10%, %, or ±25% of the value specified. For example, "about 50 percent" can in some embodiments carry a variation from 45 to 55 percent. Also for example, "about 0.5 percent" can in some embodiments carry a variation from 0.45 to 0.55 percent. For integer ranges, the term "about" can include one or two integers greater than and/or less than a recited integer.

The present disclosure is directed toward compositions, kits, and methods for the treatment and diagnosis of animals, such as domestic cats (*Felis domesticus*). One of ordinary skill will appreciate, however, that the compositions, kits, and methods disclosed herein can be equally applied to larger species of cats such as, for example, lions, jaguars, lynx, etc., dogs, farm animals, humans, other domesticated pets such as, for example, rabbits, hamsters, gerbils, or chinchillas, etc., or other mammals.

Urine specific gravity is a measurement of urine dilution. The higher the specific gravity, the more dense/concentrated the urine. The normal range for urine specific gravity in a cat is typically between 1.030 and 1.060. A very low specific gravity is indicative of renal failure, whereas a high urine specific gravity means that the urine is more concentrated and therefore it is more likely that stones will precipitate and cause problems.

Urine specific gravity is regulated by a combination of (a) urine production through glomerular filtration into the collecting ducts of the kidney and (b) resorption of water from the collecting duct to go back in to the blood stream. This process is, in part, regulated by the eicosanoid prostaglandin E2 (PGE2). PGE2 binds to prostaglandin E receptors on the kidney tubular cell and through activation of second messengers, regulates the water and sodium channels that regulate water and sodium balance in the body.

The inventors have discovered a genetic locus containing the prostaglandin E synthase 3 gene, a key enzyme in the pathway that makes PGE2 from AA, using a whole genome association study between the genotypes of cats and their individual urine specific gravity. Furthermore it has been discovered that different ratios of AA (the precursor for PGE2) to EPA+DHA in the diet of cats correlate with their urine specific gravities. Thus, it has been discovered that regulating the amount of AA in the diet can lower urine specific gravity in cats. It also has been found that even though the urine is more dilute in cats fed the composition of the present disclosure, their blood osmolality is also decreased indicating that these animals are drinking more water and that their overall water balance is increased, i.e., they are more hydrated.

A high relative super saturation ("RSS") is indicative of a propensity to form urine stones, for both oxalate and struvite stones. It has been discovered that a decline in specific gravity is correlated to a decline in RSS. Therefore, the biological benefit of a more hydrated urine in cats is a reduced risk of stone formation.

Urolithiasis management is an area of active research among many pet food manufacturers and independent researchers. The calcium oxalate titration test ("COTT"), is determined via titration of whole urine with a sodium oxalate solution until precipitation occurs. A COTT value is determined by dividing the calcium ion concentration ($[Ca^{2+}]$) by the amount of oxalate added up to the point of precipitation. COTT is also believed to also account for urine crystal inhibitors and promoters in a dog's or cat's urine. COTT testing, performed together with RSS, may bring much-needed insight into reducing the risk of calcium oxalate urolith formation in pets. This type of combined testing may also provide clinically relevant information that a specific therapy (dietary or drug) aimed at urolith risk reduction is truly reducing risk of calcium oxalate recurrence in an individual patient.

In some embodiments, a COTT value is determined using a method comprising: (a) preparing a plurality of alkali metal oxalate samples, for example in an array, wherein at least one of the samples comprises a concentration of alkali metal oxalate which is different to the concentration of alkali metal oxalate of at least one other sample; (b) reacting a known volume of a urine sample from the animal with at least one of the alkali metal oxalate samples to form calcium oxalate; (c) optionally incubating at least one sample formed in step b) with a modifier of calcium oxalate stone formation; and (d) determining the minimum concentration of alkali metal oxalate required to precipitate the calcium oxalate, wherein a lower minimum concentration of alkali metal oxalate required to precipitate the calcium oxalate is associated with a higher risk of calcium oxalate stone formation in the urinary tract of the animal In some embodiments, the concentration of alkali metal oxalate in at least one sample in step a) is less than the concentration at which saturation of alkali metal oxalate occurs. In certain embodiments, the concentration of calcium oxalate in at least one sample formed in step b) is less than the concentration at which saturation of calcium oxalate occurs.

In some embodiments, each alkali metal oxalate sample comprises an alkali metal oxalate solution, a gel comprising alkali metal oxalate, a solid alkali metal oxalate, or an alkali metal oxalate solution deposited on a surface. In some embodiments, each alkali metal oxalate sample in step a) comprises a concentration of alkali metal oxalate different from that of all other samples. In some embodiments, an array may comprise one or more groups of alkali metal oxalate samples, wherein each sample in a group comprises a concentration of alkali metal oxalate different from that of all other samples in the group.

In some embodiments, each group of alkali metal oxalate samples is a replicate of every other group. In other embodiments, each alkali metal oxalate sample is provided in a different well in a multi-well plate. In further embodiments, each well in a row of the multi-well plate comprises a different concentration of alkali metal oxalate from every other well in the row. In yet other embodiments, each well in a column of the multi-well plate comprises the same concentration of alkali metal oxalate as every other well in the column.

In some embodiments, the different concentrations of alkali metal oxalate are prepared by serial dilution of a solution of alkali metal oxalate. In some embodiments, each alkali metal oxalate sample of the array is reacted with a different aliquot of urine from a single urine sample. In some embodiments, each alkali metal oxalate sample of a group of alkali metal oxalate samples is reacted with a different aliquot of urine from a single urine sample.

In some embodiments, a plurality of urine samples is analyzed. In certain embodiments, aliquots of a first urine sample are reacted with a group of alkali metal oxalate samples, and one or more additional urine samples are each reacted with a replicate group of alkali metal oxalate samples for comparison purposes. In other embodiments, the one or more additional urine samples are collected from the same animal as the first sample. In some embodiments, the one or more additional urine samples are collected from different animals than the first sample.

In some embodiments, each aliquot of urine is provided in a different well in a multi-well plate. In some embodiments, each well in a row of the multi-well plate comprises the same concentration of a modifier of calcium oxalate stone formation as every other well in the row. In some embodiments, each well in a column of the multi-well plate comprises a different concentration of a modifier of calcium oxalate stone formation from every other well in the column.

In some embodiments, the different concentrations of modifier are prepared by serial dilution of a solution of modifier.

In some embodiments, precipitation of the calcium oxalate is determined by measuring the turbidity of the urine. In some embodiments, the turbidity of the urine is measured by determining the optical density of the urine by absorbance spectroscopy. In some embodiments, the optical density is measured at a wavelength of 585 nm. In some embodiments, precipitation of the calcium oxalate is determined by measuring the concentration of free calcium ions in the urine sample, wherein a lower concentration of free calcium ions correlates with increased precipitation of calcium oxalate.

In some embodiments, the concentration of free calcium ions in the urine sample is determined through the use of a calcium electrode able to detect the presence of calcium ions in a sample.

In some embodiments, the concentration of free calcium ions in the urine sample is estimated by adding a calcium-specific reporter dye to each sample after step c), and wherein addition of the dye causes a color change of the urine sample, and precipitation of calcium oxalate in step b) causes a reduction in the color change relative to a sample comprising no precipitated calcium oxalate resulting from a reduction in the free calcium ion concentration. In some embodiments, the calcium-specific reporter dye is fluo-3, fluo-4, fluo-4FF, fluo-5F, mag-fluo-4, fura-2, indo-1, calcium green-1, calcium orange, calcium crimson, fura red, calcein, Oregon green, rhod-1, rhod-2, rhod-3, x-rhod-5F, x-rhod, bapta-1, bapta-2, bapta-6F, dextran-linked indicators, phthalein purple, or derivatives thereof. In certain embodiments, the calcium-specific reporter dye is phthalein purple (cresolphthalein complex; 3',3"-bis[(bis(carboxymethyl)amino)methyl]-5',5'-di methyl phenol phthalein). In some embodiments, the calcium-specific reporter dye is Fluo-3, Fluo-4, fura-2, indo-1, calcium green-1, Oregon green, rhod-1, shod-2, rhod-3, rhod-5F, x-Rhod, bapta-1, bapta-2, or bapta-6F. In some embodiments, an absence of color of the sample corresponds to complete precipitation of calcium oxalate from the urine sample. In some embodiments, the alkali metal oxalate is sodium oxalate.

In some embodiments, the modifier is a salt, a metal ion, a small organic compound, an amino acid, a peptide, a protein, a nucleotide, a polynucleotide, a saccharide, an oligosaccharide, a metabolite or any combination thereof, in other embodiments, the modifier is a compound with an unknown effect on calcium oxalate stone formation. In some embodiments, the modifier is a citrate, lactate, phosphate, sulfate, carbonate, chloride, magnesium, sodium, uric acid, xanthine, cysteine, a thiazide diuretic, sodium cellulose phosphate or any combination thereof. In some embodiments, the modifier is potassium citrate.

In some embodiments, the concentration of calcium ions in the urine sample is determined prior to step b). In some embodiments, the concentration of the calcium ions is determined by spectroscopy. In some embodiments, the risk of calcium oxalate stone formation is predicted using a ratio of the concentration of calcium ions in the urine sample determined prior to step b) and the minimum amount of oxalate ions required to precipitate calcium oxalate from the urine sample.

In some embodiments, particulate matter is removed from the urine sample prior to step b). In some embodiments, the urine sample is diluted prior to step b). In some embodiments, if in step d) the animal is predicted to be at risk of calcium oxalate stone formation, a diet which reduces the risk of calcium oxalate stone formation is administered to the animal.

Some embodiments provide a method of predicting the effect of a diet on the risk, or change in risk, of calcium oxalate stone formation in the urinary tract of an animal, comprising: i) feeding the animal the diet, and ii) using any one of the methods described herein to predict the risk, or change in risk, of calcium oxalate stone formation in the urinary tract of the animal. In some embodiments, step ii) is performed before and after step i).

Other embodiments provide methods of treating an animal at elevated risk of developing calcium oxalate stone formation in the urinary tract comprising (i) identifying the animal as being at elevated risk using any one of the methods described herein, and (ii) placing the animal on a diet which reduces the risk of calcium oxalate stone formation.

In some embodiments, a kit is used to predict calcium oxalate stone formation in an animal, wherein the kit comprises: at least one alkali metal oxalate sample, wherein in certain embodiments there are multiple samples optionally comprising different concentrations of alkali metal oxalate; ii) optionally one or more modifiers of calcium oxalate stone formation; iii) optionally a container for a urine sample; iv) a means for detecting calcium ion concentration, optionally a calcium-specific reporter dye; and v) instructions for using the kit according to any one of the methods described herein. In some embodiments, the kit comprises a container comprising a plurality of wells, and each well comprises a different alkali metal oxalate sample. In some embodiments, the contents of each well is covered with a water-soluble film. In some embodiments, the alkali metal oxalate samples are deposited on a surface. In certain embodiments, the alkali metal oxalate samples are deposited in spaced-apart regions. In some embodiments, the spaced-apart regions are arranged in order of increasing concentration of alkali metal oxalate. In some embodiments, the samples are deposited to form a gradient of alkali metal oxalate concentration. In some embodiments, the surface is paper or card. In other embodiments, the surface is a thin layer chromatography plate. In some embodiments, the alkali metal oxalate deposited on the surface is covered with a water-soluble film.

In one embodiment of the kits disclosed herein, the kits comprise a container comprising multiple wells, such as a single row of wells, multiple rows of wells, or a 96-well plate. Each well may be filled first with an alkali metal oxalate in sequentially higher concentrations as one moves up the row. The alkali metal oxalate may be in solid, liquid, or gel form that includes a calcium-specific reporter dye that would bind to the free calcium in the urine. These dyes may be (but are not limited to): fluo-3, fluo-4FF, fluo-5F, mag-fluo-4, fura-2, indo-1, calcium green-1, calcium orange, calcium crimson, fura red, calcein, Oregon green, rhod-1, rhod-2, rhod-3, x-rhod-5F, x-rhod, bapta-1, bapta-2, bapta-6F, dextran-linked indicators, phthalein purple, and derivatives thereof as well as any other reporter dye that only shows color in the presence of free calcium. Each well may or may not then be covered with a thin, fast dissolving film that is soluble in water to protect the contents of each well prior to use. FIG. 8D depicts a kit comprising a single row of wells according to the embodiment described herein.

To use the kit, a known volume of urine is added to each well such that the urine comes in contact with the oxalate and free calcium-specific reporter dye. Calcium from the urine would bind to the oxalate and precipitate out of solution as calcium oxalate. Any remaining free calcium would complex with the calcium-specific reporter dye and the sample in the well would change color. The amount of oxalate required to bring about the complete precipitation of calcium (and thus the absence of color) is related to the ability of constituents of the urine to inhibit oxalate stone formation in a model system. Accordingly, urine that results in the absence of color in a well may indicate the animal is at a higher risk for oxalate stone formation than an animal whose urine achieves color in a well. In certain embodiments, the lighter the color achieved in the well, the higher the risk to the animal for calcium oxalate stone formation.

In another derivation disclosed herein, the principles discussed using wells may be translated to a multi-pad pH-style strip. In this case alkali metal oxalate (in increasing concentrations) is added to the pads of a pH style paper along with a calcium-specific reporter dye. Those pads may then optionally be covered with a thin, fast dissolving film that is soluble in water to protect the contents of each pad prior to use. In practice, the strip may be dipped into urine, and any pads that still have free calcium would change color. The amount of oxalate required to bring about the complete precipitation of calcium (and thus the absence of color) is related to the ability of constituents of the urine to inhibit oxalate stone formation in a model system. FIG. 8C depicts an embodiment comprising a multi-pad pH-style strip. In certain embodiments, the multi-pad pH-style strip may comprise multiple rows of pads, and in certain embodiments, at least one row of the strip may comprise at least one pad comprising a calcium-specific reporter dye in the absence of alkali metal oxalate. In certain embodiments, a pH-style strip may be used wherein, instead of pads, the alkali metal oxalate samples are deposited on the pH-style strip to form a gradient of alkali metal oxalate concentration.

In another derivation of embodiments disclosed herein, the principles described above may be utilized in a thin layer chromatography (TLC)-like format. Alkali metal oxalate may be deposited on a TLC plate with the concentration of the alkali metal oxalate increasing from bottom to top, such as in a gradient and as depicted in FIG. 8B. The calcium-specific reporter dye would also be embedded in this matrix. In practice, the plate may be partially dipped into a volume of urine, or, alternatively, the plate may be submerged in the urine, and the urine would migrate along the concentration gradient. At some point, the increasing concentration of oxalate would sequester all the remaining free calcium and the dye would no longer change color. The further the urine travels up the plate prior to the lack of color is related to the ability of constituents of the urine to inhibit oxalate stone formation in a model system. In certain embodiments, in lieu of a TLC plate, a capillary tube may be used, wherein the inside of the capillary tube comprises TLC matrix comprising a calcium reporter and alkali metal oxalate. In certain embodiments of the capillary tube comprising a TLC matrix, the alkali metal oxalate is deposited in the capillary tube to form a gradient of alkali metal oxalate concentration.

In a slight modification of this derivation, the alkali metal oxalate concentration is kept constant across the TLC plate, as depicted in FIG. 8A. The calcium from urine would still travel up the plate until oxalate sequestered all of it. The further the urine travels up the plate prior to the lack of color is related to the ability of constituents of the urine to inhibit oxalate stone formation in a model system.

Figure 10:
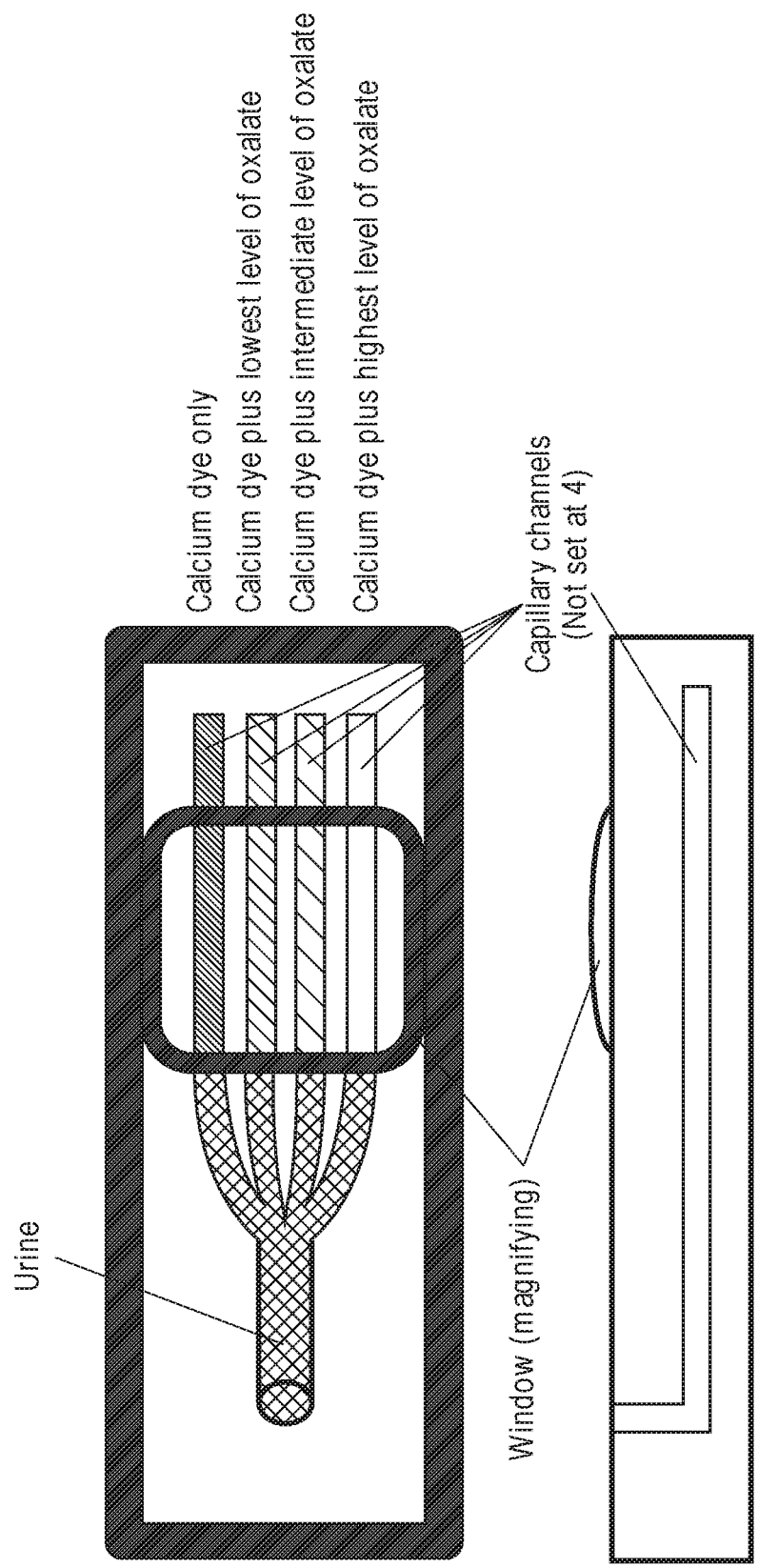
FIG. 10 depicts a multichannel plate embodiment of the kits disclosed herein.
Figure 11:
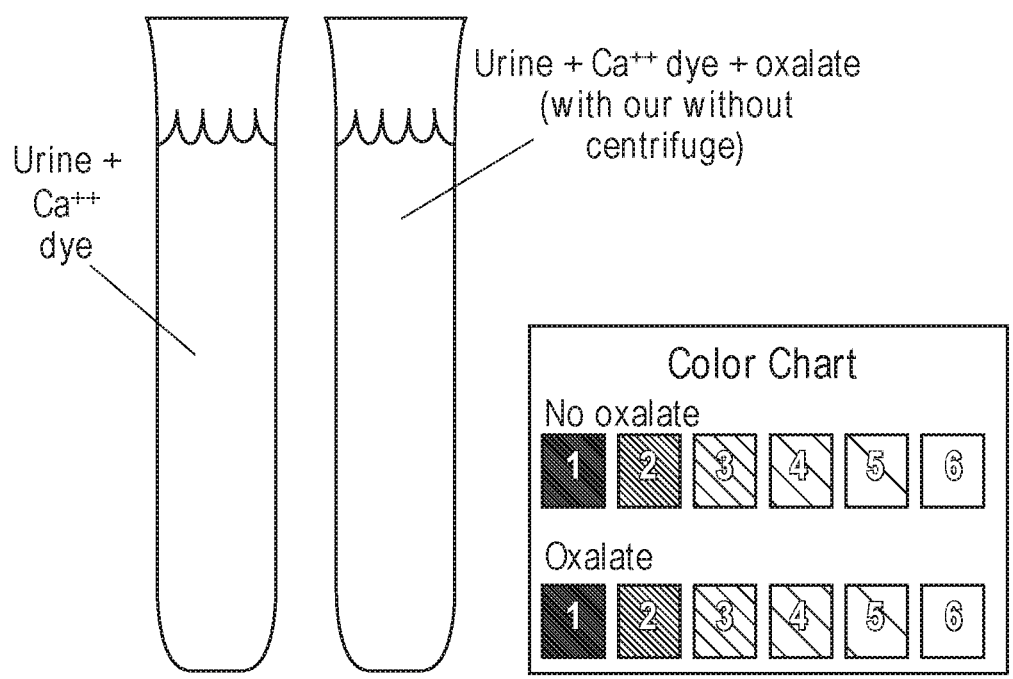
FIG. 11 depicts an embodiment of the kits disclosed herein wherein urine may be added to containers that each comprise a calcium-specific reporter dye, wherein at least one container further comprises at least one alkali metal oxalate and at least one container is substantially free of oxalate. The kit further comprises an identification chart for comparing color of urine samples added to the first and second containers, wherein the colors on the chart are colors known to be observed using a calcium-specific reporter dye for a known alkali metal oxalate concentration or the absence of alkali metal oxalate and a known concentration of free calcium ions.

In another derivation of the kits disclosed herein, the kit may comprise a multichannel plate, as depicted, for example, in FIG. 10. In certain embodiments, the multichannel plate comprises a capillary channel that comprises an opening for entry of a urine sample into the capillary channel. The capillary channel may then branch into at least two separate capillary subchannels, such as at least four separate capillary subchannels. In certain embodiments, at least one capillary subchannel may comprise the calcium-specific report dye in the absence of alkali metal oxalate, and in certain embodiments, at least one capillary subchannel may comprise the calcium-specific reporter dye and an alkali metal oxalate. In one embodiment, the capillary channel divides into at least three capillary subchannels, wherein at least one capillary subchannel comprises a calcium-specific reporter dye in the absence of alkali metal oxalate and at least two capillary subchannels comprise the calcium-specific reporter dye and alkali metal oxalate, and wherein the alkali metal oxalate is present in each capillary subchannel at a different concentration. In certain embodiments, each capillary subchannel except the capillary subchannel that is absent alkali metal oxalate comprises an increasing concentration of alkali metal oxalate. In certain embodiments, the multichannel plate may further comprise at least one magnifying window to help visualize the capillary subchannels. The calcium from urine would flow through the capillary channel into the capillary subchannels, wherein the oxalate would sequester it and the remaining free calcium would be sequestered by the calcium-specific reporter dye. The amount of oxalate required to bring about the complete precipitation of calcium (and thus the absence of color in a capillary subchannel) is related to the ability of constituents of the urine to inhibit oxalate stone formation in a model system.

In certain embodiments, there is a diagnostic kit for identifying a feline as being at elevated risk of developing a disease or condition resulting from low hydration, comprising (1) at least one first container for holding a urine sample comprising at least one calcium-specific reporter dye and substantially free of an alkali metal oxalate; (2) at least one second container for holding a urine sample comprising at least one calcium-specific reporter dye and an alkali metal oxalate sample; and (3) a chart for comparing color of urine samples added to the first and second containers, wherein the colors on the chart are colors known to be observed for an alkali metal oxalate concentration or the absence of alkali metal oxalate, a concentration of free calcium ions, and a calcium-specific reporter dye.

Figure 12:
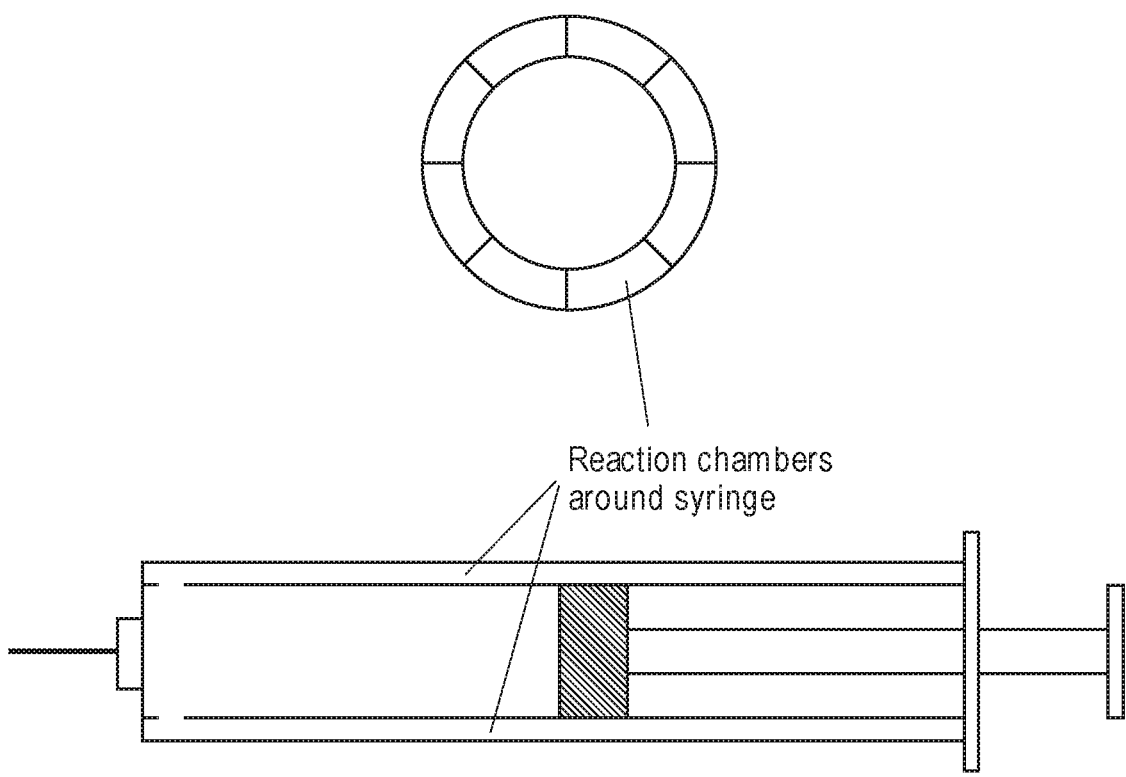
FIG. 12 depicts a cystocentesis syringe according to embodiments disclosed herein.

In yet another derivation of the kits disclosed herein, there is provided a cystocentesis syringe. An exemplary cystocentesis syringe is depicted in FIG. 12. The cystocentesis syringe disclosed herein may identify a feline as being at elevated risk of developing a disease or condition resulting from low hydration. In certain embodiments, there is provided a cystocentesis syringe for identifying a feline as being at elevated risk of developing a disease or condition resulting from low hydration, comprising: (1) an internal chamber capable of receiving a urine sample; (2) at least one reaction chamber surrounding the perimeter of the internal chamber; and (3) at least one hole between the internal chamber and the at least one reaction chamber to allow for the passage of the urine sample, where the at least one reaction chamber comprises at least one calcium-specific reporter dye. In certain embodiments, the at least one reaction chamber further comprises at least one alkali metal oxalate sample, and in certain embodiments there are at least two reaction chambers, wherein a first reaction chamber comprises at least one calcium-specific reporter dye and is substantially free of alkali metal oxalate, and wherein a second reaction chamber comprises at least one calcium-specific reporter dye and at least one alkali metal oxalate sample. In various embodiments, there are alkali metal oxalate samples deposited in the reaction chamber as a concentration gradient. In certain embodiments, the cystocentesis syringe disclosed herein further comprises at least one reaction chamber for use in identifying a disease or condition of an animal that may be identified from a urine sample from the animal. For example, in certain non-limiting embodiments, the cystocentesis syringe may comprise at least one reaction chamber for the identification of urine pH, urine sugar content, microbial presence, and/or pregnancy.

Example kits are shown in FIGS. 8-12 only for the purpose of explanation, and should not be interpreted as the only style or type.

In at least one embodiment, the compositions of the present disclosure are nutritionally, complete cat food compositions. A nutritionally complete composition provides a diet that includes sufficient nutrients for maintenance of normal health of a healthy cat. A nutritionally complete composition is palatable and, together with water, provides the sole source of all of the nutrition necessary for maintenance of normal health in a healthy cat. Nutritionally complete compositions are familiar to one of skill in the art. For example, nutrients and ingredients such as those disclosed herein as well as others suitable for animal feed compositions, and recommended amounts thereof, may be found, for example, in the Official Publication of the Associate of American Feed Control Officials ("AAFCO"), Inc., Nutrient Requirements of Dogs and Cats, 2006. For example, nutritionally complete foods can contain protein, fat, carbohydrate, dietary fiber, amino acids, minerals, vitamins, and other ingredients in amounts known by those of skill in the art.

Protein can be supplied by any of a variety of sources known by those skilled in the art, including plant sources, animal sources, or both. Animal sources include, for example, meat, meat by-products, seafood, dairy, eggs, etc. Meats include, for example, the flesh of poultry, fish, and mammals (e.g., cattle, pigs, sheep, goats, and the like). Meat by-products include, for example, lungs, kidneys, brain, livers, and stomachs and intestines (freed of all or essentially all their contents). The protein can be intact, almost completely hydrolyzed, or partially hydrolyzed. Typical protein amounts in the compositions of the present disclosure are at least about 15% (or from about 15% to about 55%, or from about 30% to about 55%, or from about 33% to about 36%).

Fat can be supplied by any of a variety of sources known by those skilled in the art, including meat, meat by-products, fish oil, and plants. Plant fat sources include wheat, flaxseed, rye, barley, rice, sorghum, corn, oats, millet, wheat germ, corn germ, soybeans, peanuts, and cottonseed, as well as oils derived from these and other plant fat sources. The compositions of the present disclosure typically contain at least about 9% (or from about 9% to about 35%, or from about 10% to about 25%, or from about 15% to about 22%) total fat.

AA can be provided from a variety of natural sources. Liver, e.g., chicken liver, is relatively high in AA. EPA also can be provided from a variety of natural sources such as, for example, fish oil. In addition to AA, EPA and DHA, fatty acids which can be included as part of the fat component in the compositions of the present invention include other omega-3 and omega-6 fatty acids such as, but not limited to, alpha-linolenic acid, gamma-linolenic acid, linoleic acid, octadecatetraenoic acid (stearidonic acid), stearic acid, palmitic acid, palmitoleic acid, oleic acid or mixtures thereof. The ratio, on a dry weight basis, of total omega-6 to total omega-3 fatty acids (n6:n3) in the compositions of the present disclosure can typically range from about 2:1 to 8:1, alternatively from about 3:1 to about 7.5:1, alternatively about 4:1 to about 7:1, and alternatively about 4.5:1 to about 6.5:1.

In some embodiments, food compositions comprising AA, EPA and DHA, the ratio of AA:(EPA+DHA) can range from about 0.1:1 to about 0.9:1, alternatively about 0.2:1 to about 0.8:1, alternatively about 0.3:1 to about 0.7:1, and alternatively about 0.4:1 to 0.6:1. Furthermore, the combined amount of AA, EPA and DHA can account for about 0.05 to about 1.5%, alternatively about 0.1 to about 1%, alternatively about 0.2 to about 0.8%, alternatively about 0.3 to about 0.7%, and alternatively 0.4 to about 0.6% of the food composition by dry weight. Food compositions comprising a ratio of AA:(EPA+DHA) less than 1:1 can be used to lower urine specific gravity and COTT value of a pet while having a lower moisture content than similar food compositions having ratios of AA:(EPA+DHA) which are considerably higher (for example, 2:1 to 5:1).

In certain embodiments, food compositions comprising AA, EPA and DHA, have an amount of AA ranging from about 0.05 to about 0.5%, alternatively from about 0.1 to about 0.3%, and alternatively from about 0.1 to about 0.2%. The combined total of EPA and DHA in the food compositions can range from about 0.1 to about 1%, alternatively from about 0.2 to about 0.8%, alternatively from about 0.3 to about 0.6%, and alternatively from about 0.3 to about 0.5%.

Carbohydrates can be supplied by any of a variety of sources known by those skilled in the art, including oat fiber, cellulose, peanut hulls, beet pulp, parboiled rice, corn starch, corn gluten meal, and any combination of those sources. Grains supplying carbohydrates can include, but are not limited to, wheat, corn, barley, and rice. Carbohydrates content of foods can be determined by any number of methods known by those of skill in the art. Generally, carbohydrate percentage can be calculated as nitrogen free extract ("NFE"), which can be calculated as follows: NFE=100%−moisture %−protein %−fat %−ash %−crude fiber %.

Dietary fiber refers to components of a plant which are resistant to digestion by an animal's digestive enzymes. Dietary fiber includes soluble and insoluble fibers. Soluble fibers are resistant to digestion and absorption in the small intestine and undergo complete or partial fermentation in the large intestine, e.g., beet pulp, guar gum, chicory root, psyllium, pectin, blueberry, cranberry, squash, apples, oats, beans, citrus, barley, or peas. Insoluble fibers can be supplied by any of a variety of sources, including, for example, cellulose, whole wheat products, wheat oat, corn bran, flax seed, grapes, celery, green beans, cauliflower, potato skins, fruit skins, vegetable skins, peanut hulls, and soy fiber. Crude fiber includes indigestible components contained in cell walls and cell contents of plants such as grains, for example, hulls of grains such as rice, corn, and beans. Typical fiber amounts in compositions of the present disclosure can be from about 0 to 10%, or about 1% to about 5%.

Amino acids, including essential amino acids, can be added to the compositions of the present disclosure as free amino acids, or supplied by any number of sources, e.g., crude protein, to the compositions of the present disclosure. Essential amino acids are amino acids that cannot be synthesized de novo, or in sufficient quantities by an organism and thus must be supplied in the diet. Essential amino acids vary from species to species, depending upon the organism's metabolism. For example, it is generally understood that the essential amino acids for dogs and cats (and humans) are phenylalanine, leucine, methionine, lysine, isoleucine, valine, threonine, tryptophan, histidine and arginine. In addition, taurine, while technically not an amino acid but a derivative of cysteine, is an essential nutrient for cats.

The compositions of the present disclosure can also contain one or more minerals and/or trace elements, e.g., calcium, phosphorus, sodium, potassium, magnesium, manganese, copper, zinc, chromium, molybdenum, selenium, or iron salts having counterions such as, for example chloride, iodide, fluoride, sulfide or oxide, in amounts required to avoid deficiency and maintain health. These amounts are known by those of skill in the art, for example, as provided in the Official Publication of the Associate of American Feed Control Officials, Inc. ("AAFCO"), Nutrient Requirements of Dogs and Cats, 2006. Typical mineral amounts are about 0.1% to about 4% or about 1% to about 2%.

The compositions of the present invention can also include vitamins in amounts required to avoid deficiency and maintain health. These amounts, and methods of measurement are known by those skilled in the art. For example, the Official Publication of the Associate of American Feed Control Officials, Inc. ("AAFCO") Nutrient Requirements of Dogs and Cats, 2006 provides recommended amounts of such ingredients for dogs and cats. As contemplated herein, vitamins can include, but are not limited to, vitamin A, vitamin $B_1$, vitamin $B_2$, vitamin $B_6$, vitamin $B_{12}$, vitamin C, vitamin D, vitamin E, vitamin H (biotin), vitamin K, folic acid, choline, inositol, niacin, and pantothenic acid. Typical vitamin amounts in the composition of the invention are about from 0 to about 3% or about 1% to about 2%.

The compositions of the present disclosure can additionally comprise other additives such as palatability enhancers and stabilizers in amounts and combinations familiar to one of skill in the art. Stabilizing substances include, for example, substances that tend to increase the shelf life of the composition. Other examples of other such additives potentially suitable for inclusion in the compositions of the invention include, for example, preservatives, colorants, antioxidants, flavorants, synergists and sequestrants, packaging gases, stabilizers, emulsifiers, thickeners, gelling agents, and humectants. Examples of emulsifiers and/or thickening agents include, for example, gelatin, cellulose ethers, starch, starch esters, starch ethers, and modified starches. The concentration of such additives in the composition typically can be up to about 5% by weight. In some embodiments, the concentration of such additives (particularly where such additives are primarily nutritional balancing agents, such as vitamins and minerals) is from about 0% to about 2.0% by weight. In some embodiments, the concentration of such additives (again, particularly, where such additives are primarily nutritional balancing agents) is from about 0% to about 1.0% by weight.

Foods of any consistency or moisture content are contemplated, e.g., the compositions of the present invention can be, for example, a dry, moist or semi-moist animal food composition. In some embodiments, the moisture content is from about 3% to about 90% of the total weight of the composition. "Semi-moist" refers to a food composition containing from about 25 to about 35% moisture. "Moist" food refers to a food composition that has a moisture content of about 60 to 90% or greater. "Dry" food refers to a food composition with about 3 to about 11% moisture content and is often manufactured in the form of small bits or kibbles.

In preparing a composition of the present invention in wet or canned form, any ingredient (e.g., AA, EPA, DHA) generally can, for example, be incorporated into the composition during the processing of the formulation, such as during and/or after mixing of other components of the composition. Distribution of these components into the composition can be accomplished by conventional means. In some embodiments, ground animal and poultry proteinaceous tissues are mixed with the other ingredients, including fish oils, cereal grains, other nutritionally balancing ingredients, special-purpose additives (e.g., vitamin and mineral mixtures, inorganic salts, cellulose and beet pulp, bulking agents, and the like); and water that is sufficient for processing is also added. These ingredients can be mixed in a vessel suitable for heating while blending the components. Heating of the mixture can be effected using any suitable manner, such as, for example, by direct steam injection or by using a vessel fitted with a heat exchanger. Following the addition of the last ingredient, the mixture can be heated to a temperature range of from about 50° F. (10° C.) to about 212° F. (100° C.). In some instances, the mixture can be heated to a temperature range of from about 70° F. (21° C.) to about 140° F. (60° C.). Temperatures outside these ranges are generally acceptable, but may be commercially impractical without use of other processing aids. When heated to the appropriate temperature, the material will typically be in the form of a thick liquid. The thick liquid can be filled into cans. When filled into cans, a lid is applied, and the container is hermetically sealed. The sealed can is then placed into conventional equipment designed to sterilize the contents. This is usually accomplished by heating to temperatures of greater than about 230° F. (110° C.) for an appropriate time, which is dependent on, for example, the temperature used and the composition.

Pet food compositions can alternatively be prepared in a dry form using conventional processes. Typically, dry ingredients, including, for example, animal protein, plant protein, grains, etc., are ground and mixed together. Moist or liquid ingredients, including fats, oils, animal protein, water, etc., are then added to and mixed with the dry mix. The mixture is then processed into kibbles or similar dry pieces. Kibble is often formed using an extrusion process in which the mixture of dry and wet ingredients is subjected to mechanical work at a high pressure and temperature; and forced through small openings and cut off into kibble by a rotating knife. The wet kibble is then dried and optionally coated with one or more topical coatings which may include; for example, flavors, fats, oils, powders, and the like. Kibble also can be made from the dough using a baking process, rather than extrusion, wherein the dough is placed into a mold before dry-heat processing.

In the methods of the present disclosure for hydrating cats or for treating a disease or condition in cats, the food administered can be a nutritionally complete cat food or the necessary amounts and ratios of AA, EPA and DHA, can be administered separately, for example, as separate ingredients or as part of a separate ingredient, typically as a supplement, so that the total diet consumed meets the amounts and ratios of AA, EPA and DHA, necessary to result in the beneficial effects of the present disclosure. In methods of the present disclosure of treating a disease or condition in a cat said disease or condition can be, for example, development of urinary stones, feline idiopathic cystitis, or FLUTD.

In some embodiments, the present invention provides a pet food composition comprising an omega-6 polyunsaturated fatty acid supplement and at least two omega-3 polyunsaturated fatty acid supplements in an amount effective to lower the calcium oxalate titration test in a feline, the diet having a greater amount of the sum of the at least two omega-3 polyunsaturated fatty acid supplements than an individual omega-6 polyunsaturated fatty acid supplement. Other embodiments provide a pet food composition comprising an omega-6 polyunsaturated fatty acid supplement and at least two omega-3 polyunsaturated fatty acid supplements in an amount effective to lower the calcium oxalate titration test in a feline, the diet having a greater amount of the sum of the at least two omega-3 polyunsaturated fatty acid supplements than the omega-6 polyunsaturated fatty acid supplement.

In some embodiments, the omega-6 polyunsaturated fatty acid supplement comprises arachidonic acid (AA) and the at least two omega-3 polyunsaturated fatty acid supplements comprise eicosapentaenoic acid (EPA) and docosahexaenoic acid (DHA). In some embodiments, the omega-6 polyunsaturated fatty acid supplement is arachidonic acid (AA) and the at least two omega-3 polyunsaturated fatty acid supplements are eicosapentaenoic acid (EPA) and docosahexaenoic acid (DHA).

Some embodiments provide the use of a composition comprising an effective amount of arachidonic acid (AA), eicosapentaenoic acid (EPA) and docosahexaenoic acid (DHA), for reducing the specific gravity of urine in a feline. Other embodiments provide the use of a composition comprising an effective amount of arachidonic acid (AA), eicosapentaenoic acid (EPA) and docosahexaenoic acid (DHA), for reducing the COTT in a feline.

In some embodiments, the present invention provides a pet food composition comprising arachidonic acid (AA), eicosapentaenoic acid (EPA) and docosahexaenoic acid (DHA), in an amount effective to reduce COTT in a feline, wherein a ratio of AA:(EPA+DHA) ranges from about 0.4:1 to about 0.6:1, and a ratio of total omega-6 fatty acids to total omega-3 fatty acids (n6:n3) ranges from about 4:1 to about 7:1.

In some embodiments, the pet food composition comprises a combined weight of AA, EPA and DHA ranging between about 0.4% to about 0.6% of the dry weight of the pet food composition.

Further embodiments provide a pet food composition comprising arachidonic acid (AA), eicosapentaenoic acid (EPA) and docosahexaenoic acid (DHA), in an amount effective to reduce the COTT in a feline, wherein a ratio of AA:(EPA+DHA) ranges from about 0.4:1 to about 0.6:1, and wherein a combined weight of AA, EPA and DHA is about 0.4% to about 0.6% of the dry weight of the pet food composition.

Yet other embodiments provide a method of improving the hydration level in a feline comprising providing the feline with a diet comprising an effective amount of an omega-6 polyunsaturated fatty acid supplement and at least two omega-3 polyunsaturated fatty acid supplements, wherein the diet reduces the COTT in said feline.

In some embodiments, the pet food composition, or diet based thereon, reduces the COTT by at least 10%. In other embodiments, the pet food composition, or diet based thereon, reduces the COTT by at least 25%.

In other embodiments, the level of hydration is improved to an extent sufficient to treat a disease or condition selected from urinary stones, feline idiopathic cystitis, and FLUTD.

Still further embodiments provide a method of maintaining or achieving homeostatic levels of hydration in a feline, comprising providing a diet comprising an effective amount of an omega-6 polyunsaturated fatty acid supplement and at least two omega-3 polyunsaturated fatty acid supplements to a feline in need thereof.

The invention is further described in the following examples. The examples are merely illustrative and do not in any way limit the scope of the invention as described and claimed.

EXAMPLES

Example 1

Described below in Table 1 are four (4) comparative formulas, and three (3) exemplary, formulas of the present invention.

TABLE 1

| | Comparative Examples | | | | Examples | | |
|---|---|---|---|---|---|---|---|
| | Comp. Ex. 1 | Comp. Ex. 2 | Comp. Ex. 3 | Comp. Ex. 4 | Ex. 1 | Ex. 2 | Ex. 3 |
| Component | | | w/w % (dry) | | | | |
| Crude Protein | 37.15 | 33.78 | 33.75 | 32.17 | 33.85 | 33.6 | 34.16 |
| Fat | 18.02 | 23.71 | 14.65 | 17.38 | 19.93 | 16.49 | 16.70 |
| Crude Fiber | 3.32 | 2.16 | 2.14 | 3.24 | 0.99 | 0.92 | 1.79 |
| Calcium | 0.95 | 1.19 | 1.86 | 1.41 | 0.76 | 0.71 | 0.84 |
| Phosphorus | 0.73 | 1.02 | 1.33 | 1.18 | 0.58 | 0.53 | 0.75 |
| Ash | 5.46 | 6.7 | 8.08 | 8.14 | 5.72 | 5.42 | 5.56 |
| Leucine | 4.03 | 2.43 | 2.9 | 2.54 | 2.94 | 3.2 | 3.8 |
| Isoleucine | 1.27 | 0.97 | 0.89 | 0.89 | 1.12 | 1.07 | 1.30 |
| Lysine | 2.35 | 1.79 | 1.31 | 1.44 | 1.76 | 1.61 | 1.45 |
| Methionine | 1.42 | 1.11 | 0.75 | 1.12 | 0.98 | 0.77 | 0.95 |
| Cystine | 0.52 | 0.38 | 0.46 | 0.41 | 0.74 | 0.74 | 0.48 |
| n-3 fatty acids* | 0.64 | 0.52 | 0.25 | 0.41 | 0.81 | 0.6 | 0.46 |
| n-6 fatty acids* | 3.52 | 4.38 | 2 | 3.69 | 3.95 | 3.52 | 3.01 |
| n6:n3 | 5.5:1 | 8.4:1 | 8:1 | 9:1 | 4.9:1 | 5.8:1 | 6.5:1 |
| AA | 0.09 | 0.15 | 0.05 | 0.1 | 0.17 | 0.17 | 0.16 |
| EPA + DHA | 0.35 | 0.12 | 0.09 | 0.17 | 0.37 | 0.36 | 0.27 |
| AA:(EPA + DHA) | 0.26 | 1.25 | 0.56 | 0.59 | 0.46 | 0.48 | 0.59 |
| AA + EPA + DHA | 0.44 | 0.27 | 0.14 | 0.27 | 0.54 | 0.53 | 0.43 |

*Value represents total amount of fatty acids in the formula.

Example 2

A feeding study was conducted to assess the impact of diet on COTT. Twelve (12) cats were fed a control diet and twelve (12) cats were fed a test diet having a low AA:(EPA+DHA) ratio according to the present disclosure. The control diet contained 0.07 wt % AA and 0.02 wt % of EPA and DHA combined, yielding an AA:(EPA+DHA) ratio of 3.5:1, and a moisture content of 5.15 wt %. The test diet contained 0.16 wt % AA and 0.27 wt % of EPA and DHA combined, yielding an AA:(EPA+DHA) ratio of 0.59:1, and a moisture content of 5.11 wt %. The cats were maintained on their respective diets for fifty-six (56) days.

Urine from each cat was collected and analyzed at day A, day B and day C. Over the feeding period, the cats fed the control diet exhibited an average COTT value of 54.5. During this same time, the cats fed the test diet, according to certain embodiments of the present invention, exhibited an average COTT value of 40.2. As illustrated by this example, cats fed with the test diet exhibited a 26% reduction in the risk of calcium oxalate stone formation.

Example 3

A feeding study was conducted to assess the impact of diet on urine specific gravity. Twelve (12) cats were fed the control diet of Example 1 and twelve (12) cats were fed the test diet of Example 1. The cats were maintained on their respective diets for fifty-six (56) days. Urine from each cat was collected and analyzed for urine specific gravity at day zero (0), day twenty-eight (28) and day fifty-six (56). During this feeding period, the cats fed the control diet exhibited an average urine specific gravity of 1.056. During the same time, the cats fed the test diet according to the present disclosure, exhibited an average urine specific gravity of 1.053. As illustrated by this example, cats fed with the test diet exhibited urine which was less concentrated (i.e. less dense) despite being fed a diet with 0.04 wt % less moisture than the control diet.

Example 4

Oxalate only method. Oxalate is placed into the first column (8 wells) of a 96-well microliter plate, and serially diluted across the rows. In the example shown in FIG. 1, 300 μL of 250 mM oxalate is placed in the first column, while 150 μL of vehicle is placed into all other wells. Then, 150 μL of the oxalate solution from the first column is removed and combined with the 150 μL of vehicle in the second column. After mixing, this process is repeated across the plate making the oxalate more dilute in each column by a factor of two (2).

In a separate plate, 100 μL of a mammal's clarified urine is placed into each well. Then, 100 μL of the serially diluted oxalate is added to the urine plate while maintaining the oxalate dilution positions (e.g. R1:C1 from the oxalate plate is placed into R1:C1 of the urine plate).

After mixing, precipitation of calcium oxalate is assessed in a plate reader set to emit 585 nm light. There is a positive correlation between the absorbance at this wavelength and the amount of precipitate in each well.

Experimental Results

The urine samples from eight cats were used to assess the ability of this method to distinguish between cats that were shown to be resistant to oxalate stone formation from those that were shown to have little or no resistance. Urine was collected separately for each cat in specially designed litter trays for 24 hours. These urine samples were then used to derive COTT results using the traditional titration method, and also by this 96 well method. Plates were set up in duplicate as described in the oxalate only method. The data shown in Table 2 below are the average values of the two plates.

TABLE 2

| Plate setup expt 1 | | | | | | | | | | | | |
|---|---|---|---|---|---|---|---|---|---|---|---|---|
| mM oxalate (final concentration) | | | | | | | | | | | | |
| Andrew | 125 | 62.5 | 31.3 | 15.63 | 7.81 | 3.91 | 1.95 | 0.98 | 0.49 | 0.24 | 0.12 | 0.06 |
| Corn Pop | 125 | 62.5 | 31.3 | 15.63 | 7.81 | 3.91 | 1.95 | 0.98 | 0.49 | 0.24 | 0.12 | 0.06 |
| Wells | 125 | 62.5 | 31.3 | 15.63 | 7.81 | 3.91 | 1.95 | 0.98 | 0.49 | 0.24 | 0.12 | 0.06 |
| Marie | 125 | 62.5 | 31.3 | 15.63 | 7.81 | 3.91 | 1.95 | 0.98 | 0.49 | 0.24 | 0.12 | 0.06 |
| Maverick | 125 | 62.5 | 31.3 | 15.63 | 7.81 | 3.91 | 1.95 | 0.98 | 0.49 | 0.24 | 0.12 | 0.06 |
| Pdawn | 125 | 62.5 | 31.3 | 15.63 | 7.81 | 3.91 | 1.95 | 0.98 | 0.49 | 0.24 | 0.12 | 0.06 |
| Honey Cluster | 125 | 62.5 | 31.3 | 15.63 | 7.81 | 3.91 | 1.95 | 0.98 | 0.49 | 0.24 | 0.12 | 0.06 |
| Cadbury | 125 | 62.5 | 31.3 | 15.63 | 7.81 | 3.91 | 1.95 | 0.98 | 0.49 | 0.24 | 0.12 | 0.06 |
| Data expt 1 | | | | | | | | | | | | |
| Plate reader | | | | | | | | | | | | |
| Andrew | 0.086 | 0.093 | 0.089 | 0.085 | 0.087 | 0.088 | 0.090 | 0.084 | 0.085 | 0.086 | 0.093 | 0.089 |
| Corn Pop | 0.081 | 0.081 | 0.078 | 0.075 | 0.086 | 0.079 | 0.077 | 0.074 | 0.075 | 0.077 | 0.087 | 0.077 |
| Wells | 0.165 | 0.157 | 0.153 | 0.138 | 0.121 | 0.118 | 0.119 | 0.123 | 0.119 | 0.120 | 0.120 | 0.115 |
| Marie | 0.136 | 0.142 | 0.129 | 0.118 | 0.114 | 0.114 | 0.105 | 0.100 | 0.108 | 0.110 | 0.115 | 0.106 |
| Maverick | 0.150 | 0.153 | 0.138 | 0.123 | 0.124 | 0.122 | 0.122 | 0.121 | 0.123 | 0.126 | 0.128 | 0.127 |
| Pdawn | 0.164 | 0.146 | 0.138 | 0.133 | 0.095 | 0.075 | 0.073 | 0.076 | 0.076 | 0.076 | 0.086 | 0.073 |
| Honey Cluster | 0.145 | 0.133 | 0.126 | 0.118 | 0.128 | 0.126 | 0.123 | 0.124 | 0.120 | 0.124 | 0.132 | 0.129 |
| Cadbury | 0.117 | 0.117 | 0.115 | 0.094 | 0.098 | 0.095 | 0.102 | 0.091 | 0.099 | 0.094 | 0.097 | 0.092 |

The oxalate plate was set up such that 125 mM oxalate was placed into the first well and serially diluted across the plate. Once 100 μL of these oxalate solutions were diluted into 100 μL urine, the final oxalate concentrations were as described in the "plate setup expt 1" figure above. After mixing, the absorbance was quantified at 585 nm, resulting in the "Data expt 1" in Table 2 above, and the graph shown in FIG. 3. Data for this graph was generated by normalizing to the first absorbance data point for each cat.

Figure 3:
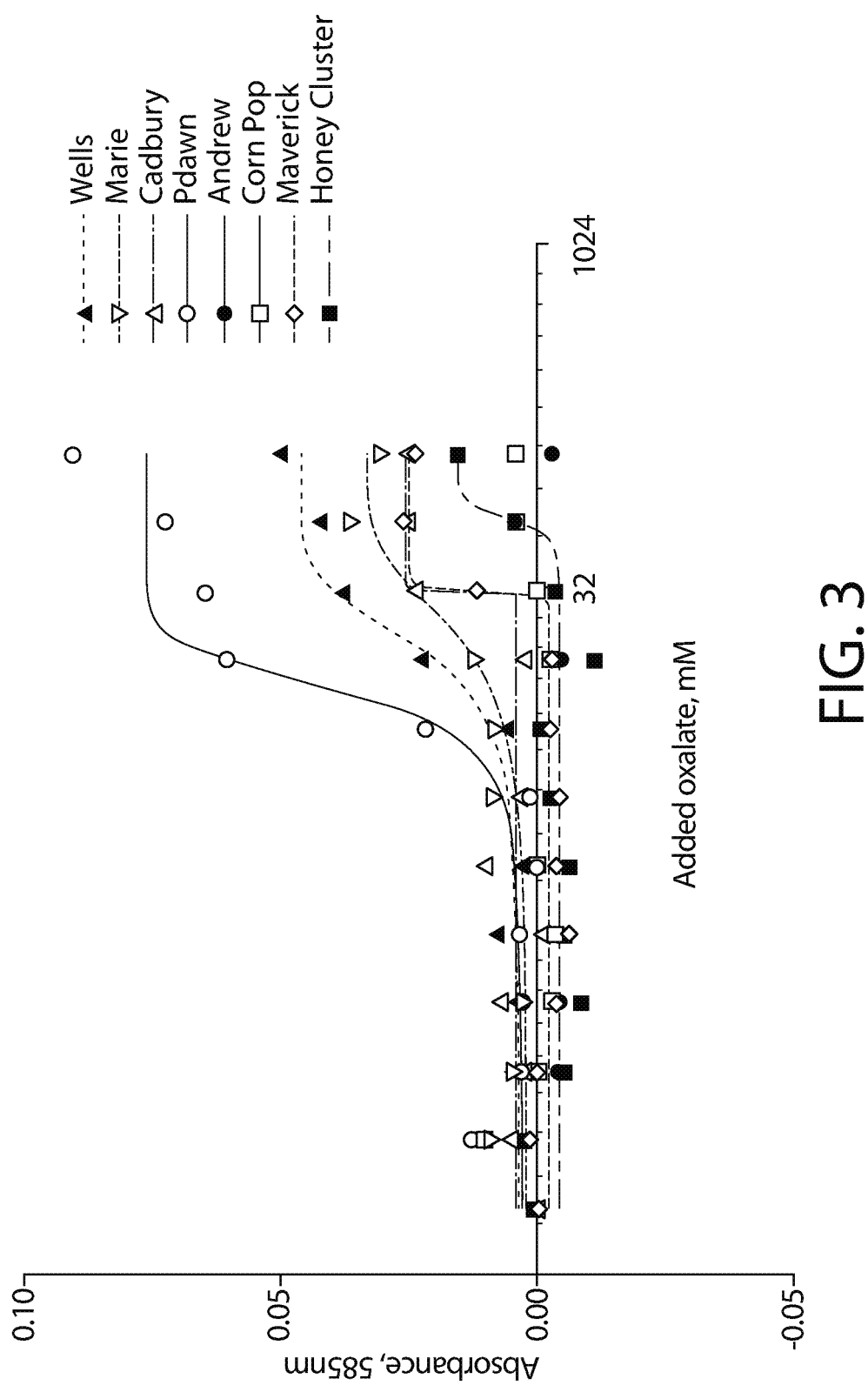
FIG. 3 shows a plot of absorbance of the urine of 8 different cats at 585 nm versus the concentration of oxalate added to the urine.
Figure 4:
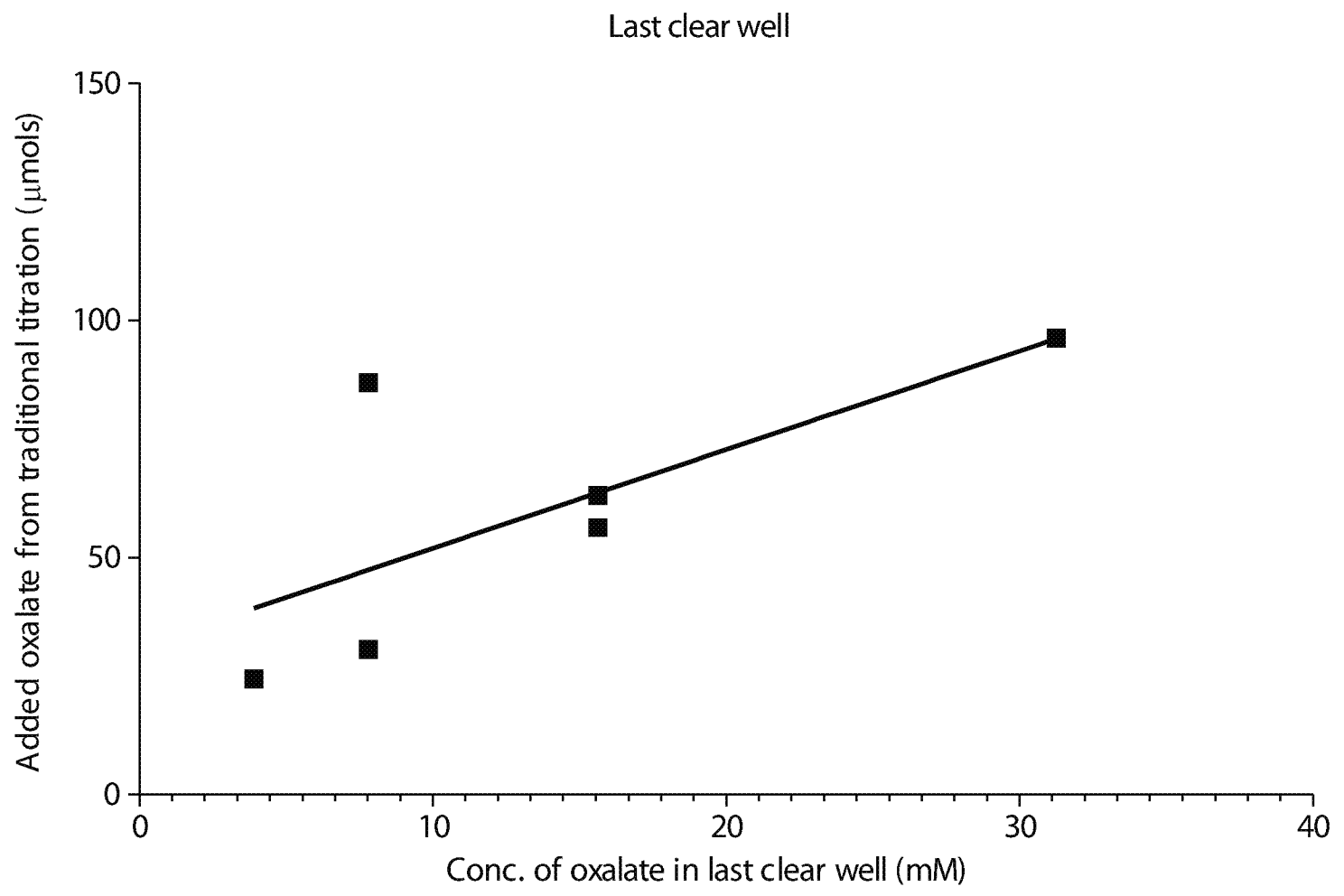

Using the graph shown in FIG. 3, the point at which precipitation started was determined, and the well just before this one is defined as the last clear well ("LCW"). Comparing the concentration of oxalate in the LCW to the concentration of oxalate that caused precipitation in the traditional titration method gave good correlation between the two methods (see FIG. 4). It is also possible to fit the data to a curve (for example a sigmoid) and mathematically determine the inflection point where precipitation starts.

A second study was run in order to confirm the results of the first. Two plates were run where most of the cats were duplicates. In several instances, a cat was only represented once. Data are presented in Table 3 below. The plate setups were done according to the method described above.

TABLE 3

| | mM oxalate (final concentration) | | | | | | | | | | | |
|---|---|---|---|---|---|---|---|---|---|---|---|---|
| | Plate setup 1 expt 2 | | | | | | | | | | | |
| Honey Cluster | 125 | 62.5 | 31.3 | 15.63 | 7.81 | 3.91 | 1.95 | 0.98 | 0.49 | 0.24 | 0.12 | 0.06 |
| Elrod | 125 | 62.5 | 31.3 | 15.63 | 7.81 | 3.91 | 1.95 | 0.98 | 0.49 | 0.24 | 0.12 | 0.06 |
| Andrew | 125 | 62.5 | 31.3 | 15.63 | 7.81 | 3.91 | 1.95 | 0.98 | 0.49 | 0.24 | 0.12 | 0.06 |
| Marie | 125 | 62.5 | 31.3 | 15.63 | 7.81 | 3.91 | 1.95 | 0.98 | 0.49 | 0.24 | 0.12 | 0.06 |
| Wells | 125 | 62.5 | 31.3 | 15.63 | 7.81 | 3.91 | 1.95 | 0.98 | 0.49 | 0.24 | 0.12 | 0.06 |
| Maverick | 125 | 62.5 | 31.3 | 15.63 | 7.81 | 3.91 | 1.95 | 0.98 | 0.49 | 0.24 | 0.12 | 0.06 |
| Corn Pop | 125 | 62.5 | 31.3 | 15.63 | 7.81 | 3.91 | 1.95 | 0.98 | 0.49 | 0.24 | 0.12 | 0.06 |
| Arlette | 125 | 62.5 | 31.3 | 15.63 | 7.81 | 3.91 | 1.95 | 0.98 | 0.49 | 0.24 | 0.12 | 0.06 |
| | Plate setup 2 expt 2 | | | | | | | | | | | |
| Ardella | | | | | | | | | | | | |
| Algott | 125 | 62.5 | 31.3 | 15.63 | 7.81 | 3.91 | 1.95 | 0.98 | 0.49 | 0.24 | 0.12 | 0.06 |
| Pdawn | 125 | 62.5 | 31.3 | 15.63 | 7.81 | 3.91 | 1.95 | 0.98 | 0.49 | 0.24 | 0.12 | 0.06 |
| Arlette | 125 | 62.5 | 31.3 | 15.63 | 7.81 | 3.91 | 1.95 | 0.98 | 0.49 | 0.24 | 0.12 | 0.06 |
| Marie | 125 | 62.5 | 31.3 | 15.63 | 7.81 | 3.91 | 1.95 | 0.98 | 0.49 | 0.24 | 0.12 | 0.06 |
| Wells | 125 | 62.5 | 31.3 | 15.63 | 7.81 | 3.91 | 1.95 | 0.98 | 0.49 | 0.24 | 0.12 | 0.06 |
| Maverick | 125 | 62.5 | 31.3 | 15.63 | 7.81 | 3.91 | 1.95 | 0.98 | 0.49 | 0.24 | 0.12 | 0.06 |
| Elrod | 125 | 62.5 | 31.3 | 15.63 | 7.81 | 3.91 | 1.95 | 0.98 | 0.49 | 0.24 | 0.12 | 0.06 |
| | 125 | 62.5 | 31.3 | 15.63 | 7.81 | 3.91 | 1.95 | 0.98 | 0.49 | 0.24 | 0.12 | 0.06 |

Figure 5:
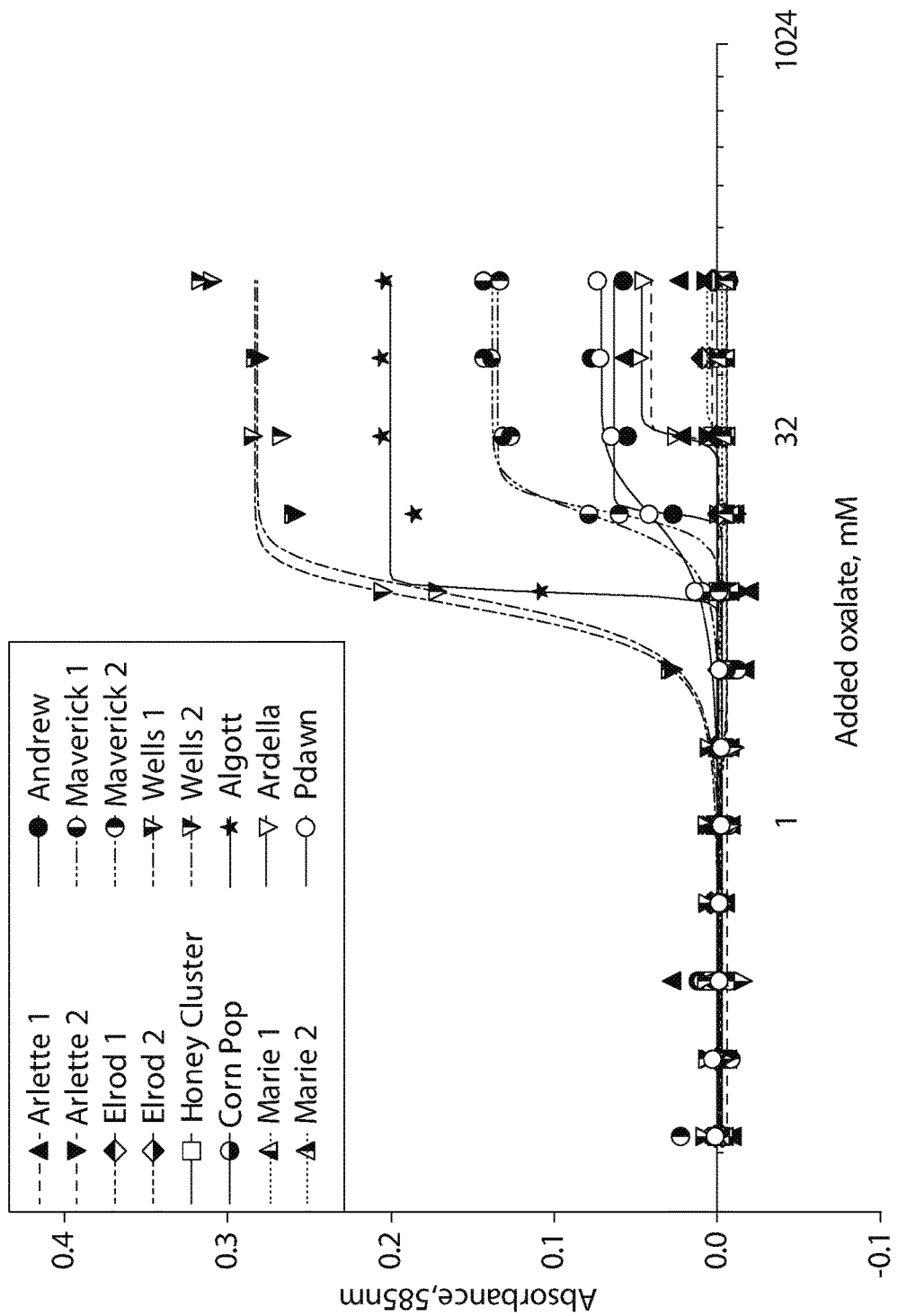
FIG. 5 shows a plot of absorbance of the urine of different cats at 585 nm versus the concentration of oxalate added to the urine.

Data from both plates are provided in Table 4 and FIG. 5. This time, data for graphs were normalized to the first 3 data points.

TABLE 4

| | Plate reader | | | | | | | | | | | |
|---|---|---|---|---|---|---|---|---|---|---|---|---|
| | Data expt 2 plate 1 | | | | | | | | | | | |
| Honey Cluster | 0.096 | 0.105 | 0.103 | 0.096 | 0.101 | 0.094 | 0.101 | 0.101 | 0.100 | 0.104 | 0.099 | 0.100 |
| Elrod | 0.073 | 0.079 | 0.070 | 0.069 | 0.067 | 0.068 | 0.071 | 0.070 | 0.073 | 0.069 | 0.068 | 0.066 |
| Andrew | 0.151 | 0.171 | 0.149 | 0.121 | 0.087 | 0.083 | 0.088 | 0.091 | 0.092 | 0.105 | 0.090 | 0.089 |
| Marie | 0.093 | 0.094 | 0.093 | 0.091 | 0.091 | 0.094 | 0.095 | 0.098 | 0.098 | 0.105 | 0.098 | 0.095 |
| Wells | 0.455 | 0.427 | 0.430 | 0.404 | 0.351 | 0.173 | 0.151 | 0.152 | 0.152 | 0.130 | 0.141 | 0.154 |
| Maverick | 0.305 | 0.300 | 0.293 | 0.240 | 0.171 | 0.156 | 0.156 | 0.156 | 0.162 | 0.161 | 0.164 | 0.165 |
| Corn Pop | 0.080 | 0.082 | 0.082 | 0.080 | 0.082 | 0.082 | 0.083 | 0.086 | 0.085 | 0.097 | 0.084 | 0.083 |
| Arlette | 0.157 | 0.190 | 0.155 | 0.122 | 0.113 | 0.116 | 0.125 | 0.124 | 0.128 | 0.161 | 0.126 | 0.124 |
| | Data expt 2 plate 2 | | | | | | | | | | | |
| Ardella | 0.169 | 0.172 | 0.149 | 0.123 | 0.122 | 0.119 | 0.129 | 0.128 | 0.124 | 0.122 | 0.122 | 0.122 |
| Algott | 0.328 | 0.330 | 0.330 | 0.310 | 0.233 | 0.122 | 0.125 | 0.127 | 0.124 | 0.122 | 0.123 | 0.124 |
| Pdawn | 0.161 | 0.160 | 0.153 | 0.130 | 0.102 | 0.087 | 0.085 | 0.085 | 0.087 | 0.087 | 0.091 | 0.089 |
| Arlette | 0.149 | 0.149 | 0.148 | 0.130 | 0.127 | 0.132 | 0.134 | 0.143 | 0.140 | 0.137 | 0.147 | 0.142 |
| Marie | 0.100 | 0.105 | 0.101 | 0.100 | 0.102 | 0.103 | 0.104 | 0.104 | 0.104 | 0.106 | 0.105 | 0.102 |
| Wells | 0.518 | 0.485 | 0.469 | 0.461 | 0.373 | 0.231 | 0.191 | 0.193 | 0.197 | 0.209 | 0.208 | 0.202 |
| Maverick | 0.364 | 0.373 | 0.357 | 0.290 | 0.229 | 0.218 | 0.223 | 0.223 | 0.230 | 0.223 | 0.222 | 0.253 |
| Elrod | 0.079 | 0.083 | 0.078 | 0.074 | 0.075 | 0.077 | 0.077 | 0.076 | 0.077 | 0.077 | 0.078 | 0.079 |

Figure 6:
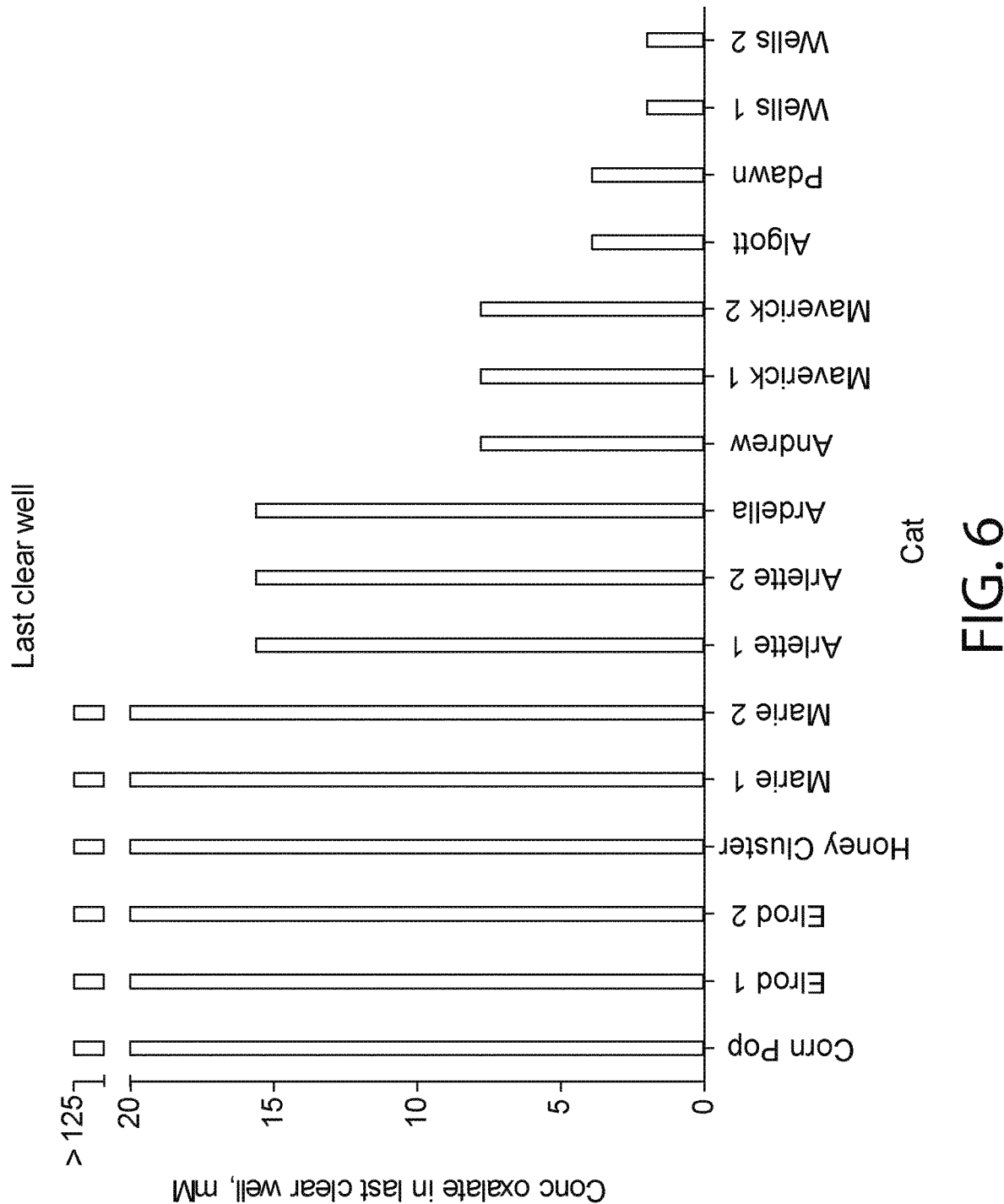
FIG. 6 is a chart showing the concentration of oxalate in the last clear well for each cat in the experiment of Example 5.

In this second experiment there were a number of cats that had a clear final well (See FIG. 6). Because it would not be possible to determine where the LCW would fall, those cats were excluded from further calculations.

Figure 7:
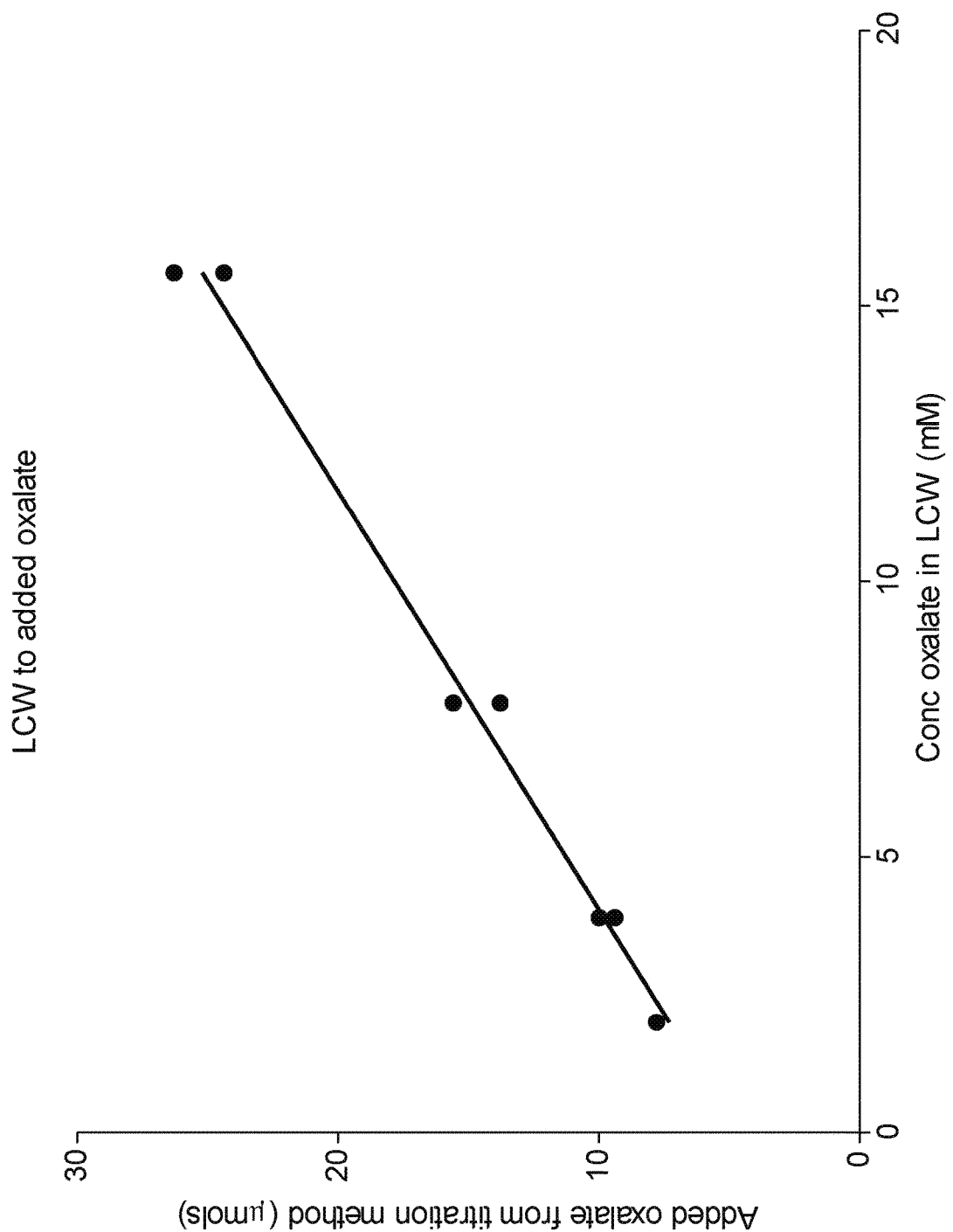
FIG. 7 shows a plot demonstrating the correlation between the amount of oxalate added in a traditional titration method and the concentration of oxalate in the last clear well in the method of the invention.
Figure 9:
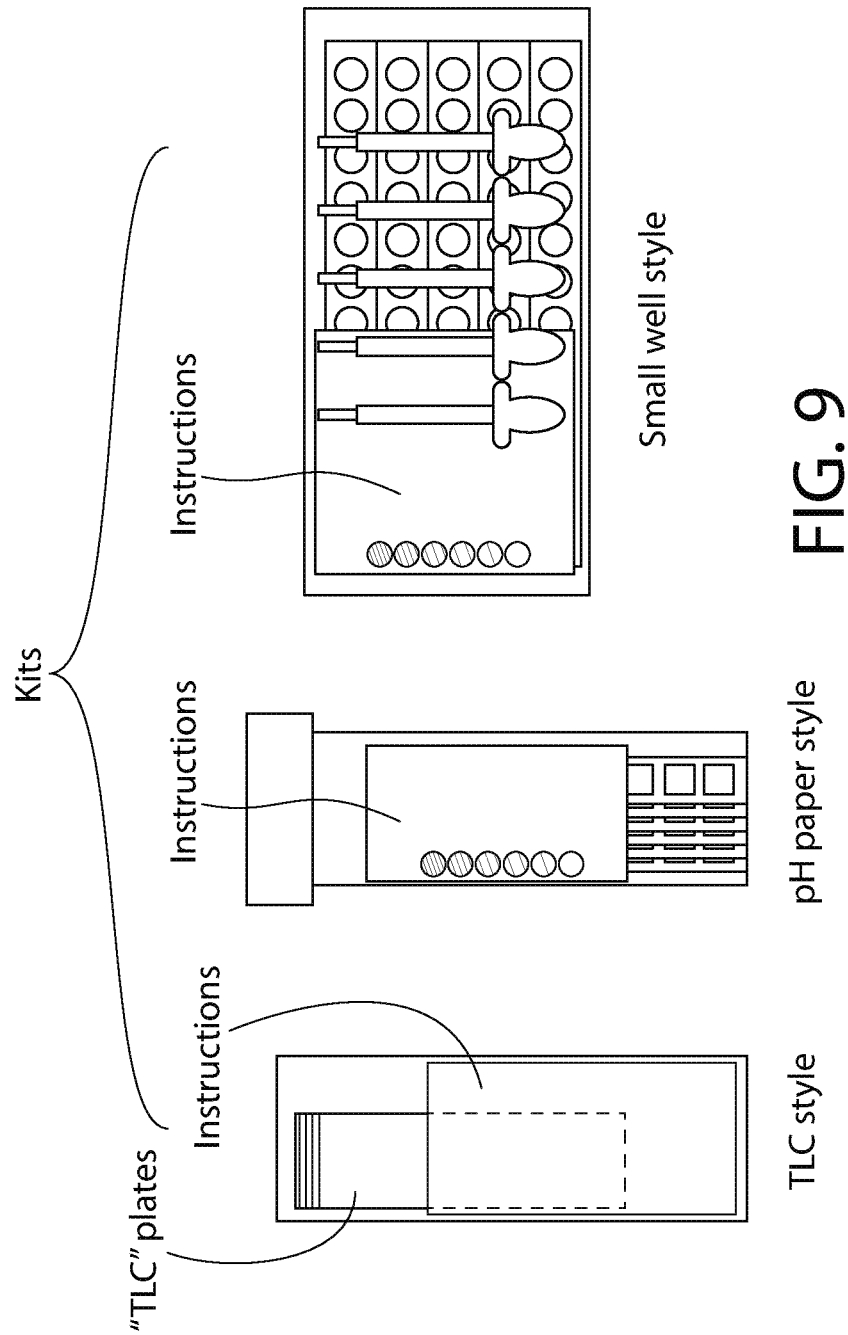
FIG. 9 is a schematic of the TLC, pH paper and small well embodiments of the kits of the present invention.

Using FIG. 5, the point at which precipitation started was determined, and the well just before this one is defined as the LCW. Comparing the concentration of oxalate in the LCW to the concentration of oxalate that caused precipitation in the traditional COTT gave excellent correlation between methods (see Table 5 and FIG. 7).

TABLE 5

|  | Conc. oxalate in last clear well, mM | Added Oxalate from traditional titration, µmol |
|---|---|---|
| Corn Pop * | 125 | 50.0 |
| Elrod 1 * | 125 | 25.0 |
| Elrod 2 * | 125 | 23.8 |
| Honey Cluster * | 125 | 27.5 |
| Marie 1 * | 125 | 38.8 |
| Marie 2 * | 125 | 42.5 |
| Maverick 1 | 7.8 | 13.8 |
| Maverick 2 | 7.8 | 13.8 |
| Pdawn | 3.9 | 10.0 |
| Wells 1 | 2 | 6.3 |
| Wells 2 | 2 | 7.5 |
| Algott | 3.9 | 10.0 |
| Andrew | 7.8 | 13.8 |
| Ardella | 15.6 | 27.5 |
| Arlette 1 | 15.6 | 25.0 |
| Arlette 2 | 15.6 | 23.8 |

* The well with the highest concentration of oxalate was clear. Therefore it was unknown how much further the resistance to precipitation would have gone. As a result, the use of these data would be untrustworthy, and were therefore excluded from further calculations Example 5

Figure 2A:
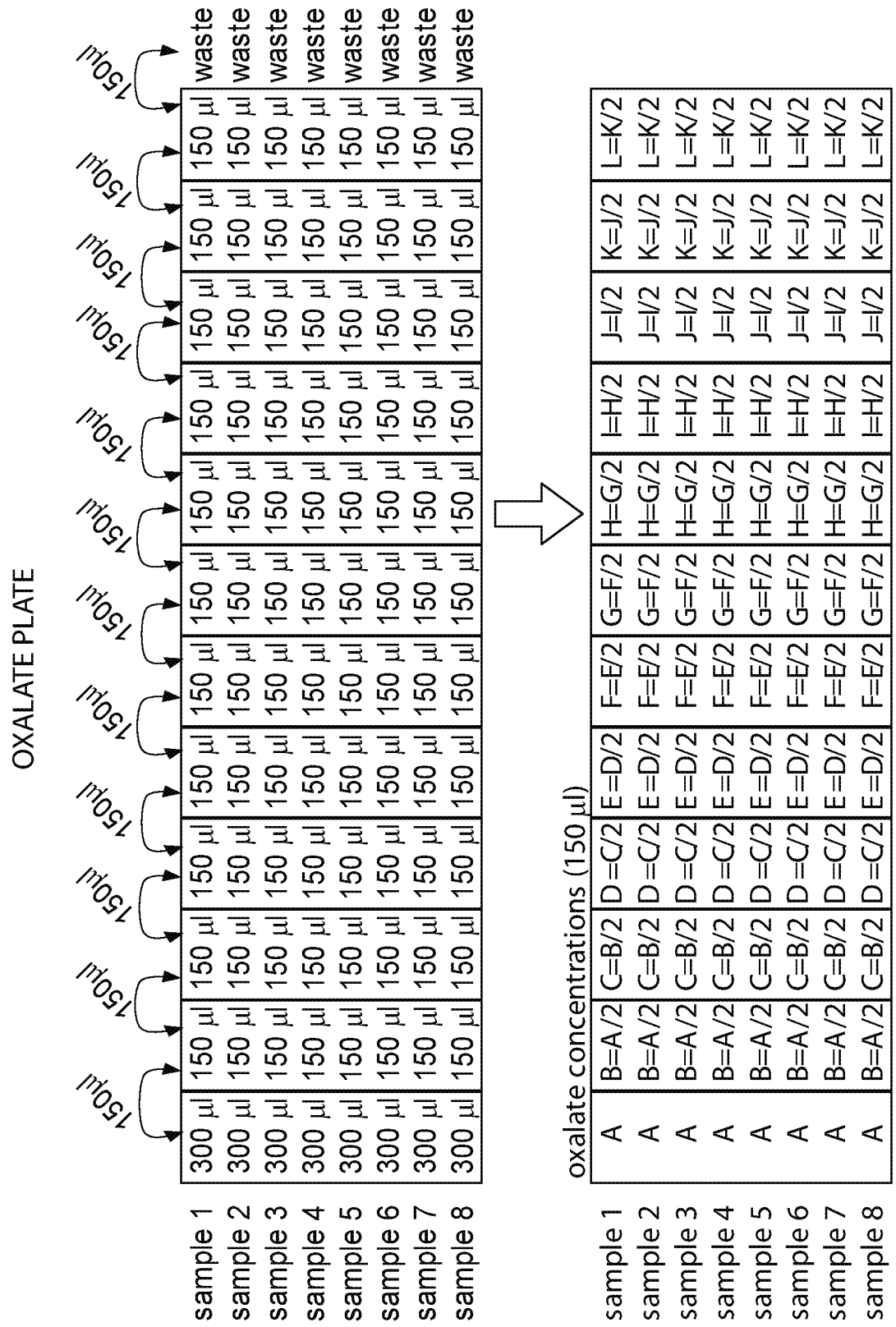
FIG. 2A depicts an embodiment of the invention wherein a multi-well plate comprising a number of alkali metal oxalate solutions comprising different concentrations of alkali metal oxalate are prepared by serial dilution of an alkali metal oxalate solution across the rows of wells of the multi-well plate.
Figure 2B:
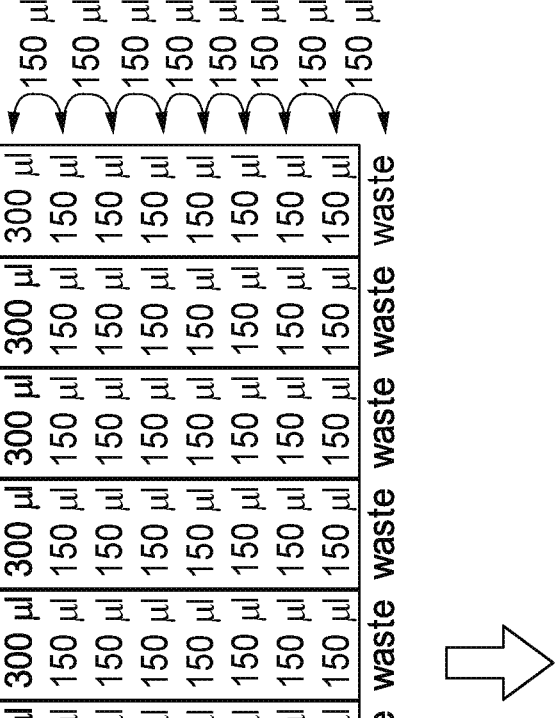
FIG. 2B depicts a multi-well plate comprising a number of solutions, for example citrate solutions comprising different concentrations of citrate prepared by serial dilution of a citrate solution down the columns of wells of the multi-well plate.

Oxalate plus secondary constituent method. In order to assess the effect of other constituents of urine that may have influence on the resistance to oxalate stone formation, a similar assay can be run, but with oxalate serially diluted in one dimension, and a constituent of interest serially diluted in a second dimension. FIG. 2 illustrates the assessment of citrate on the resistance to oxalate stone formation, but this same principle can be used for any secondary substance of interest.

An oxalate plate is prepared as described above. A second plate is prepared with the substance of interest (e.g. citrate). However in this case, the serial dilutions are done down the columns of the plate instead of across the rows. A third plate is used for the urine as above.

To 100 µL of urine is added 100 µL of from the serially diluted constituent plate while maintaining the constituent dilution positions (e.g. R1:C1 from the constituent plate is placed into R1:C1 of the urine plate). After mixing, 100 µL of the serially diluted oxalate is added to the urine plate while maintaining the oxalate dilution positions (e.g. R1:C1 from the oxalate plate is placed into R1:C1 of the urine plate). After a second mixing, precipitation of calcium oxalate is assessed in a plate reader set to emit 585 nm light. There is a positive correlation between the absorbance at this wavelength and the amount of precipitate in each well.

With this general format one may envision the ability to not only detect resistance to calcium oxalate stone formation, but also be able to test potential secondary inhibitors of stone formation by placing the test compound in decreasing (or increasing) concentrations across the rows of the same 96 well plate. In this way, plates for assessing both oxalate and a potential secondary inhibitor of interest (e.g. citrate) may be generated. It is also envisioned that one may test the resistance to other potential binary urinary stones, such as $CaCO_3$, and $CaPO_4$, as well as ternary urinary stones such as magnesium ammonium phosphate stones.

In practice, a known volume of urine would be placed in all of the wells of a clean 96 well plate. After creating a new plate of secondary inhibitor of interest (e.g. citrate) by diluting the concentration of this inhibitor down the rows of its own plate, a known volume of inhibitor from this plate is added to the urine plate and mixed, maintaining the inhibitor dilution positions (e.g. R1:C1 from the inhibitor plate is placed into R1:C1 of the urine plate). An oxalate plate is also created using the method described above, and the oxalate is then added to the urine+secondary inhibitor plate maintaining the oxalate dilution positions (e.g. R1:C1 from the oxalate plate is placed into R1:C1 of the urine/inhibitor plate). The degree of calcium oxalate precipitation is then quantified using the absorbance method described above, allowing the determination of the effect of oxalate and a secondary inhibitor on the inhibition calcium oxalate stone formation in a model system.

Given the success of these experiments, it was determined that this same principle could also be applied to testing kits that could be used in a laboratory or clinic setting. In addition, several different formats were evaluated. These kits would allow the assessment of the risk of oxalate stone formation and the outcome of treatment. Several non-limiting examples are discussed above. The actual design may be different (e.g. the order of addition, the amounts of each constituent, etc.).

While particular embodiments have been chosen to illustrate the invention, it will be understood by those skilled in the art that various changes and modifications can be made therein without departing from the scope of the invention as defined in the appended claims. Persons of ordinary skill in the art will readily appreciate that various combinations of the features depicted in the different views may be possible in some non-limiting embodiments of the present invention.

In addition, all references cited herein are hereby incorporated by reference in their entireties. In the event of a conflict in a definition in the present disclosure and that of a cited reference, the present disclosure controls.

What is claimed is:

1. A diagnostic kit for identifying an animal as being at an elevated risk of developing a disease or condition resulting from low hydration, comprising:
   at least one alkali metal oxalate sample that may be contacted with urine from the animal;
   a means for detecting calcium ion concentration in the at least one alkali metal oxalate sample;
   at least one modifier of calcium oxalate comprising a citrate; and
   instructions for using the kit.

2. The diagnostic kit according to claim 1, wherein the disease or condition resulting from low hydration is Feline Lower Urinary Tract Diseases (FLUTD), wherein the FLUTD is the formation of calcium oxalate stones.

3. The diagnostic kit according to claim 1, wherein a first of the at least one alkali metal oxalate sample comprises a different concentration of alkali metal oxalate from a second of the at least one alkali metal oxalate sample.

4. The diagnostic kit according to claim 1, wherein the at least one alkali metal oxalate sample is sodium oxalate.

5. The diagnostic kit according to claim 1, wherein the at least one modifier of calcium oxalate stone formation is potassium citrate.

6. The diagnostic kit according to claim 1, wherein the means for detecting calcium ion concentration is at least one calcium-specific reporter dye, wherein the calcium-specific reporter dye comprises one or more of fluo-3, fluo-4, fluo-4FF, fluo-5F, mag-fluo-4, fura-2, indo-1, calcium green-1, calcium orange, calcium crimson, fura red, calcein, Oregon green, rhod-1, rhod-2, rhod-3, x-rhod-5F, x-rhod, bapta-1, bapta-2, bapta-6F, dextran-linked indicators, phthalein purple, derivatives thereof, or combinations thereof.

7. The diagnostic kit according to claim 6, wherein the calcium-specific reporter dye comprises phthalein purple.

8. The diagnostic kit according to claim 1, wherein the at least one alkali metal oxalate sample is deposited in wells of a well plate or on a surface.

9. The diagnostic kit according to claim 8, wherein the at least one alkali metal oxalate sample is deposited on the surface, and wherein the at least one alkali metal oxalate sample is deposited on spaced-apart regions of the surface or in a concentration gradient on the surface.

10. The diagnostic kit according to claim 1, wherein the at least one alkali metal oxalate sample and the means for detecting calcium ion concentration are in capillary channels of a multichannel plate, and wherein the capillary channels of the multichannel plate are interconnected to a channel for receiving a urine sample.

11. The diagnostic kit according to claim 10, wherein at least one capillary channel of the multichannel plate comprises the means for detecting calcium ion concentration and is substantially free of alkali metal oxalate.

12. A diagnostic kit for identifying an animal as being at elevated risk of developing a disease or condition resulting from low hydration, comprising:
  at least one container for holding a urine sample comprising at least one calcium-specific reporter dye and substantially free of an alkali metal oxalate;
  at least one container for holding a urine sample comprising at least one calcium-specific reporter dye, at least one modifier of calcium oxalate comprising a citrate, and an alkali metal oxalate sample; and
  a chart for comparing color of urine samples added to the first and second containers, wherein the colors on the chart are colors known to be observed for an alkali metal oxalate concentration or the absence of alkali metal oxalate, a concentration of free calcium ions, and a calcium-specific reporter dye.

13. A method for predicting the risk of calcium oxalate stone formation in the urinary tract of an animal, the method comprising:
  preparing a plurality of alkali metal oxalate samples, wherein at least one sample comprises a concentration of alkali metal oxalate that is different from a concentration of alkali metal oxalate of at least one other sample;
  incubating at least one sample formed with a modifier of calcium oxalate comprising a citrate;
  reacting a known volume of a urine sample from the animal with the alkali metal oxalate samples; and
  determining a minimum concentration of alkali metal oxalate required to precipitate calcium oxalate, wherein a lower minimum concentration of alkali metal oxalate required to precipitate the calcium oxalate is associated with a higher risk of calcium oxalate stone formation in the urinary tract of the animal.

14. The method according to claim 13, wherein the minimum concentration of alkali metal oxalate required to precipitate calcium oxalate is determined with a calcium-specific reporter dye.

15. The method according to claim 14, wherein the calcium-specific reporter dye is phthalein purple.

* * * * *